(12) United States Patent
Vitello et al.

(10) Patent No.: US 7,819,847 B2
(45) Date of Patent: Oct. 26, 2010

(54) SYSTEM AND METHODS FOR ADMINISTERING BIOACTIVE COMPOSITIONS

(75) Inventors: Christopher John Vitello, Corvallis, OR (US); Stephen R. Welkley, Corvallis, OR (US); Andrew L Evans, Philomath, OR (US); John C. Greeven, Sant Cugat del Valles (ES)

(73) Assignee: Hewlett-Packard Development Company, L.P., Houston, TX (US)

( * ) Notice: Subject to any disclaimer, the term of this patent is extended or adjusted under 35 U.S.C. 154(b) by 1304 days.

(21) Appl. No.: 11/228,884

(22) Filed: Sep. 16, 2005

(65) Prior Publication Data
US 2006/0031099 A1  Feb. 9, 2006

Related U.S. Application Data

(63) Continuation-in-part of application No. 10/459,065, filed on Jun. 10, 2003, now Pat. No. 7,442,180.

(60) Provisional application No. 60/618,933, filed on Oct. 13, 2004.

(51) Int. Cl.
*A61M 5/14* (2006.01)
*A61M 31/00* (2006.01)

(52) U.S. Cl. .......................... 604/253; 604/65

(58) Field of Classification Search ............ 604/65–67, 604/131, 253; 128/DIG. 12, DIG. 13
See application file for complete search history.

(56) References Cited

U.S. PATENT DOCUMENTS

| | | | |
|---|---|---|---|
| 3,604,419 A * | 9/1971 | Diskin et al. .............. 604/31 |
| 3,737,251 A | 6/1973 | Berman | |
| 3,874,826 A | 4/1975 | Lundquist | |
| 3,985,133 A | 10/1976 | Jenkins | |
| 4,335,835 A | 6/1982 | Beigler | |
| 4,557,725 A | 12/1985 | Heyne | |
| 4,583,975 A | 4/1986 | Pekkarinen | |
| 4,683,481 A | 7/1987 | Johnson | |
| 4,786,803 A | 11/1988 | Majette | |
| 4,835,435 A | 5/1989 | Yeung | |
| 4,857,048 A | 8/1989 | Simons | |
| 4,872,028 A | 10/1989 | Lloyd | |
| 4,922,268 A | 5/1990 | Osborne | |
| 4,990,932 A | 2/1991 | Houston | |
| 4,992,808 A | 2/1991 | Bartky | |
| 5,278,584 A | 1/1994 | Keefe | |
| 5,419,684 A | 5/1995 | Struble | |
| 5,420,627 A | 5/1995 | Keefe | |
| 5,512,046 A | 4/1996 | Pusinelli | |
| 5,881,716 A | 3/1999 | Wirch | |

(Continued)

FOREIGN PATENT DOCUMENTS

EP  0 824 022  2/1998

(Continued)

*Primary Examiner*—Manuel A Mendez

(57) ABSTRACT

Bioactive agents are dosed by a jet dispenser using inkjet technology, such as that used in printing devices. A controller may control delivery of one or more drugs, timing of drug administration, or change drug regimens in response to a changing medical condition of a patient or information received from other nodes in a healthcare system. In a healthcare system, smart devices coupled to healthcare nodes can be in communication with the controller for controlling the administration of bioactive compositions from the jet dispenser.

50 Claims, 17 Drawing Sheets

U.S. PATENT DOCUMENTS

| | | | |
|---|---|---|---|
| 5,894,841 A | 4/1999 | Voges | |
| 5,960,085 A * | 9/1999 | de la Huerga | 340/5.61 |
| 6,123,861 A | 9/2000 | Santini | |
| 6,149,968 A | 11/2000 | Shimada | |
| 6,186,619 B1 | 2/2001 | Usui | |
| 6,193,343 B1 | 2/2001 | Norigoe | |
| 6,270,478 B1 | 8/2001 | Mernoe | |
| 6,474,786 B2 | 11/2002 | Percin | |
| 6,530,640 B1 | 3/2003 | Vega | |
| 6,684,880 B2 * | 2/2004 | Trueba | 128/200.16 |
| 2003/0065294 A1 | 4/2003 | Pickup | |

FOREIGN PATENT DOCUMENTS

| | | |
|---|---|---|
| EP | 0 985 420 | 3/2000 |
| EP | 1 306 219 | 5/2003 |
| WO | WO 99/10830 | 3/1999 |
| WO | WO 00/16981 | 3/2000 |
| WO | WO 02/11049 | 2/2002 |
| WO | WO 03/094075 | 11/2003 |

\* cited by examiner

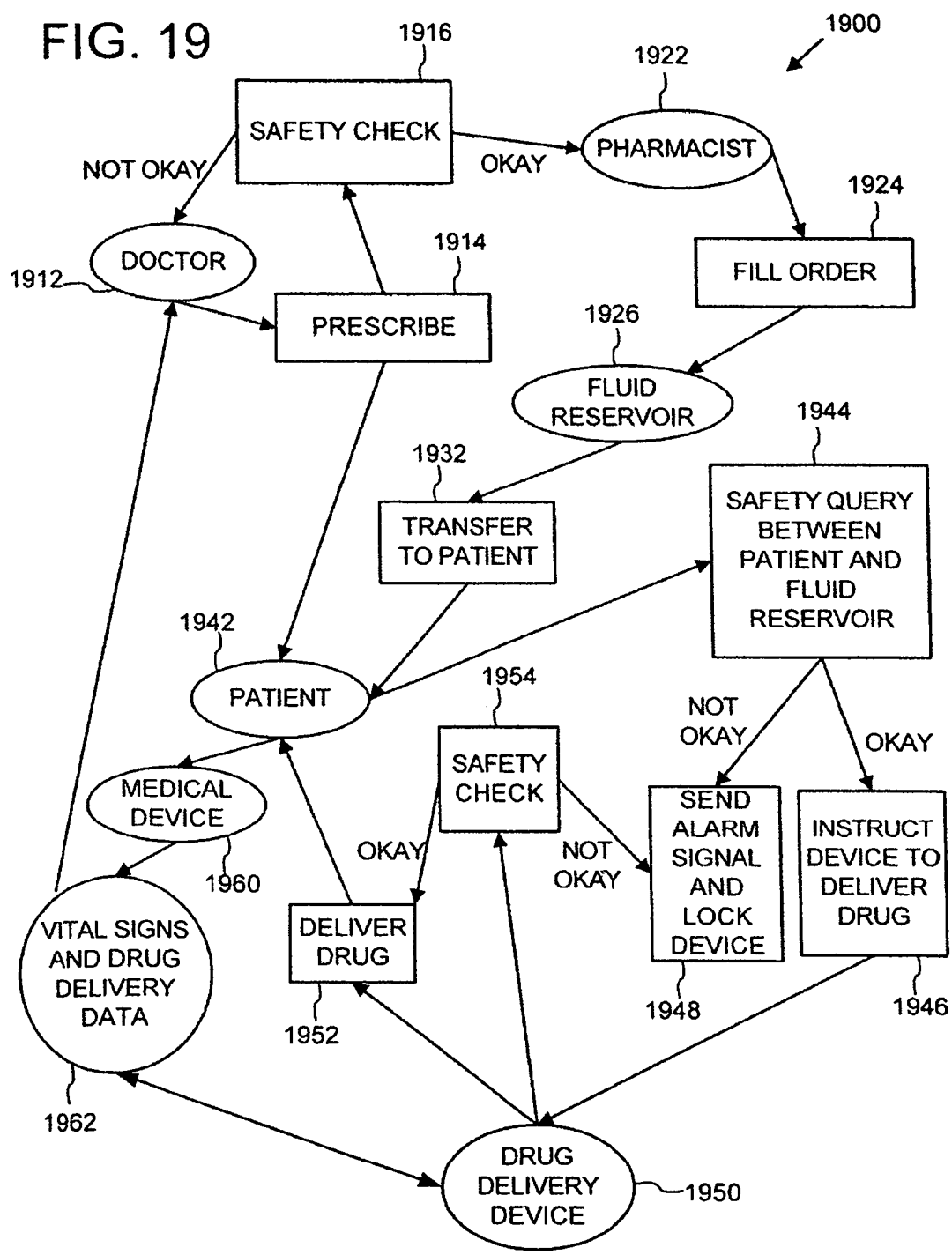

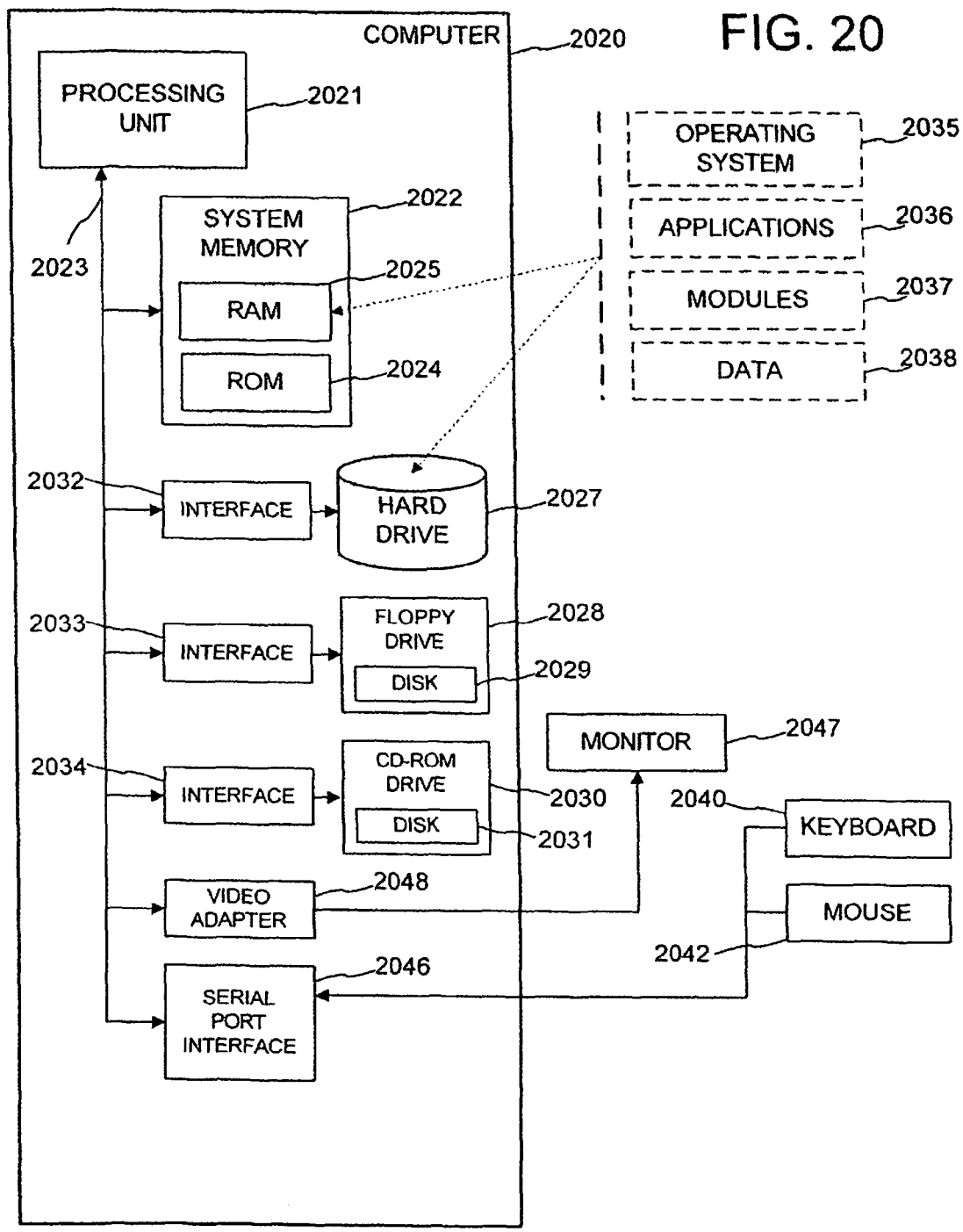

SYSTEM AND METHODS FOR ADMINISTERING BIOACTIVE COMPOSITIONS

CROSS-REFERENCE TO RELATED APPLICATION

This application is a continuation-in-part of U.S. patent application Ser. No. 10/459,065 filed Jun. 10, 2003 now U.S. Pat. No. 7,442,180. In addition, this application claims the benefit and priority of U.S. Provisional Application No. 60/618,933, filed on Oct. 13, 2004, and titled SYSTEMS AND METHODS FOR ADMINISTERING BIOACTIVE COMPOSITIONS.

FIELD

This invention relates to methods for the administration of compositions (such as pharmaceutical compositions), including compositions administered via infusion. The invention also relates to the operation of a healthcare system in which compositions are administered to patients using inkjet-based drug delivery devices (e.g. drug delivery devices employing thermal inkjet type or piezoelectric inkjet type dispensers). In particular, this invention combines the unrelated technologies of pharmaceutical administration, inkjet technology, and smart devices.

BACKGROUND

In hospitals and other medical facilities, it is often necessary to administer medication to a patient by infusing the medication into the patient through a catheter that is connected to the circulatory system of the patient, for example by infusion into a blood vessel. A common infusion technique involves introducing into the patient a solution containing a medication and an infusion liquid, which serves as a diluent for the medication. In some instances, the medication can be supplied directly to the patient without an infusion liquid. An infusion can involve dispensing the fluid to the subject by gravity or actively pumping the fluid into the subject using a device known as an infusion pump.

Unfortunately, current systems for administering drugs by way of infusion suffer from several disadvantages. For example, the mechanical components of infusion pumps are prone to wear, which can make it difficult to accurately control the volumetric amount of fluid supplied to the subject.

Furthermore, safety is a major issue in the healthcare industry with respect to the ordering, mixing and delivery of drugs to patients. Fully-interconnected devices in healthcare settings can reduce the potential for human error, provide closed loop feedback and control, and improve the safety and reliability of existing systems. Interconnected devices can ensure that medical professionals are provided real-time data for making rapid data-based decisions. Such interconnectivity can also improve patient safety and allow for patient-specific real-time variable drug administration.

Unfortunately, currently there are few fully interconnected devices in the healthcare industry. Such existing systems commonly include the use of paper-based communications in heathcare facilities and in the systems which order and deliver medications to patients. Electronic systems do exist in the healthcare industry, but are often targeted towards specific areas such as the pharmacy or doctor-patient interactions. Computerized physician order entry (CPOE) is a computerized based system used by physicians to place orders for medications and tests. Electronic medical record (EMR) systems can be used as one way to store information in one common system.

One of the leading technologies used to improve safety in the healthcare field is barcoding. Barcoding can be used to enable matching of patients with the proper medications in a hospital or healthcare setting. Unfortunately, barcoding is not a smart technology. A barcode has no ability to record, process, receive or output data in real-time. Data can be placed within the barcode, but it must be read and interpreted by scanning devices and software. Barcoding requires extra medical professional hours because a reader must be used to manually scan in the barcodes attached to patients, drugs, and other healthcare nodes. Also, because barcoding systems are dependent on human interaction, this can lead to errors in scanning and add extra stress to a system all ready under intense pressure.

Finally, time is a major issue in the healthcare field. With a shortage of medical professionals, improving efficiency is important to retaining workers and reducing costs. Insufficient time and heavy paperwork demands can prevent medical professionals from providing needed quality, safe clinical care. Current systems commonly used in medical settings generate wasted materials due to inefficiency and paper overload. Such systems create safety problems, such as matching the right drug to the right patient and making sure the drug is administered through the right route at the right time and in the proper dosage. Additionally, such systems create problems for adjusting drug dosage for patients once the drug has been delivered to the patient's room. With shelf-life limitations and an inability to react real-time to changes, drugs are often disposed of if the incorrect drug is delivered to the room or if the drug dosage needs to be changed. This adds to the cost of healthcare systems and reduces the quality of care.

In the busy medical profession where safety is vital and the administration of drugs is a common safety concern, there is a need for fully interconnected healthcare systems. Devices, systems and methods are disclosed herein for improving the administration of drugs and the operation of healthcare systems.

SUMMARY

Embodiments described herein include systems and methods for accurately administering a bioactive composition to a patient and for operating a healthcare system in which bioactive compositions are administered. For example, information can be sent from one or more healthcare nodes within a healthcare system to a smart device on or within a drug delivery device having a jet dispenser. This enables real-time synchronization of data and records with the drug-delivery device and other healthcare nodes, such as medical professionals, computer systems, fluid reservoirs, or medical devices. Constantly refreshing, updating, and storing data and records ensures healthcare professionals, devices, and computer systems within the healthcare system have the most up to date information for generating instructions for the administration of a drug, making decisions regarding the health of a patient, and creating a health history for the patient for later analysis.

Safety can be improved through such information transfer with checks and balances integrated into the system. Real-time data communicated between healthcare nodes in a healthcare system enables healthcare professionals to monitor patient drug delivery and response. With up to date information, drug delivery devices can automatically, or via interaction with a healthcare professional, adjust drug administration accordingly. The systems and methods disclosed herein can ensure that the right drug is given to the right patient through the right route (i.e. through the correct healthcare system route, the correct healthcare device, and/or the correct access into the body) at the right time and at the right dosage.

Additional features and advantages of the invention will be made apparent from the following detailed description of illustrated embodiments, which proceeds with reference to the accompanying drawings.

BRIEF DESCRIPTION OF THE DRAWINGS

FIG. 19 is a flowchart showing an exemplary implementation of a system and method for operating a healthcare system.

FIG. 20 is a block diagram of an exemplary computer system that can be implemented with the described technologies.

DETAILED DESCRIPTION

Figure 1:
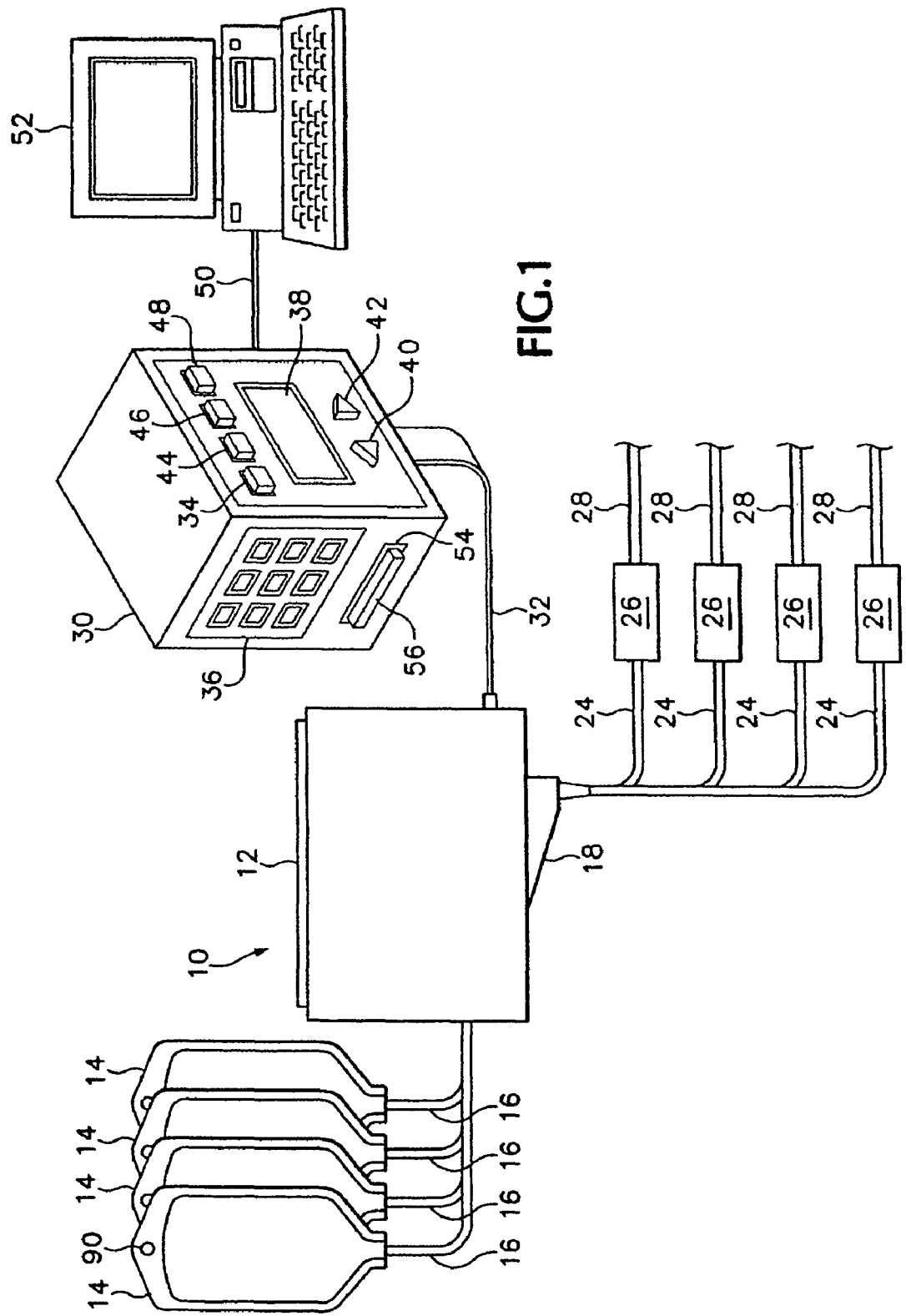
FIG. 1 is an overall schematic view of one embodiment of an infusion system for simultaneously administering multiple medications to a subject.

Unless otherwise noted, technical terms are used according to conventional usage. Definitions of common terms in pharmacology may be found in *Remington: The Science and Practice of Pharmacy*, 19$^{th}$ Edition, published by Mack Publishing Company, 1995 (ISBN 0-912734-04-3).

The singular forms "a," "an," and "the" refer to one or more than one, unless the context clearly dictates otherwise.

As used herein, the term "comprises" means "includes."

As used herein, a group of individual members stated in the alternative includes embodiments relating to a single member of the group or combinations of multiple members. For example, the term "antibiotic, bronchodilator, or vitamin," includes embodiments relating to "antibiotic," "bronchodilator," "vitamin," "antibiotic and bronchodilator," "bronchodilator and vitamin," "antibiotic and vitamin," and "antibiotic, bronchodilator, and vitamin."

A "bioactive" composition, substance, or agent is a composition that affects a biological function of a subject to which it is administered. An example of a bioactive composition is a pharmaceutical substance, such as a drug or antibiotic, which is given to a subject to alter a physiological condition of the subject, such as a disease. Bioactive substances, compositions, and agents also include other biomolecules, such as proteins and nucleic acids, or liposomes and other carrier vehicles that contain bioactive substances. Bioactive compositions also may include pharmaceutical carriers, adjuvants, and salts.

"Drug" includes any bioactive composition administered for a therapeutic (including diagnostic) purpose.

As used herein, the term "infusion" refers to the introduction of a fluid into a subject, such as the intravascular, intramuscular, intraorbital, subcutaneous, intrahepatic, intralymphatic, or intrathecal introduction of a fluid. The infusion can include flowing or dripping the fluid into the subject by gravity or pumping the fluid into the subject with the aid of a pump. An "infusion liquid" includes any fluid, such as water or a saline solution, that is mixed with a drug and infused into a subject.

As used herein, the term "jet dispenser" refers to a fluid dispenser having a construction similar to an inkjet dispenser used in inkjet printing technology. The construction of the jet dispensers in the disclosed embodiments can be modified from a conventional inkjet construction to accommodate, for example, the characteristics of the particular fluid to be dispensed. In the embodiments disclosed herein, the jet dispenser can be, for example, a piezoelectric inkjet type dispenser or a thermal inkjet type dispenser, which are further discussed below.

As used herein, the term "smart device" refers to any device which can receive, store, and send information, and optionally analyze information. For example, a smart device can be a computer system, smart card or the like.

As used herein, the term "smart card" refers to a small electronic device that can include memory including read-only and/or random-access memory, an integrated circuit including a central processing unit, communication capabilities including wireless networking capabilities, or any combination thereof. Smart card can also refer to devices that include Dynamic Data Authentication (DDA) and similar encrypted and password-type "smart" technologies. Such devices are common to the credit card and banking industries to ensure secure transactions and correct identification.

As used herein, the term "healthcare node" refers to any component of a healthcare system. For example, a healthcare node can include human subjects, medical devices, bioactive composition containers, computer systems, businesses, departments, and the like.

According to one aspect, the present disclosure concerns systems and methods for accurately dosing a bioactive composition in infusions. In particular embodiments, a dispensing apparatus for dosing a bioactive composition includes a jet dispenser, such as a thermal jet dispenser or a piezoelectric jet dispenser, having a construction similar to an inkjet dispenser used in inkjet printing technology. The jet dispenser propels precise amounts of the bioactive composition in the form of small droplets into a fluid manifold, in which the droplets mix with an infusion liquid. The fluid manifold has a fluid inlet for receiving the infusion liquid and an outlet for discharging a solution of the infusion liquid and the bioactive composition into a fluid conduit, such as a catheter, for delivery to a subject. The solution may be allowed to flow directly into a subject by gravity. Alternatively, the solution may be fed to a pump for applying a positive pressure to the solution to facilitate infusion of the solution into the subject.

In one representative embodiment, a dispensing apparatus includes a plurality of jet dispensers and a fluid manifold having a plurality of mixing chambers. Each jet dispenser is operable to dispense a controlled amount of a bioactive composition into a respective mixing chamber. Each mixing chamber has an inlet for receiving an infusion liquid to be mixed with the bioactive composition and an outlet for discharging a mixture of the infusion liquid and the bioactive composition. In certain embodiments, the dispensing apparatus has a plurality of fluid reservoirs for containing and delivering the bioactive composition to the jet dispensers. The fluid reservoirs can be separate components, or alternatively, the fluid reservoirs can be a series of individual spaces or compartments formed within an integral fluid reservoir unit.

The dispensing apparatus also may include a controller for manually or automatically dispensing the bioactive substance from the dispenser at selected times and at specified rates. The controller may take the form of an actuator that is manually depressed to activate the dispenser and dispense the agent. Alternatively, the controller may be a programmable device, such as a microprocessor, that is programmed to dispense the bioactive agent at predetermined intervals, for example several times a day. In yet another embodiment, the controller may be a computer system or smart device, such as a smart chip or the like. In some embodiments, the controller includes an audible or visible cue, such as a tone or light, to alert the subject that a dose of the bioactive composition is ready to be dispensed. Alternatively, the controller may be used to adjust the dosage of an administered drug for a particular circumstance, such as a particular time of day, an event (such as an activity that will require a dosage modification), or detection of a physiological condition (such as an adverse drug reaction that requires reduction or cessation of drug administration). Complex administration protocols may be followed, for example applying different drugs at different times throughout the day or for longer periods, such as a week, a month, or even longer. In embodiments in which smart devices are used, administration protocols can be determined in real-time due to the communication between the controller smart device and smart devices coupled to other healthcare nodes within a healthcare system.

Using existing inkjet technology, exact dosing of the drug may be achieved. Controllers may be used to dispense simple or complex drug regimens, which is of particular advantage in patients who require numerous daily medications. Computerized control of medication dosing, which may be programmed by medical personnel for subsequent automated delivery or may be adjusted on-the-fly due to updated information received from other healthcare nodes, can help avoid toxic drug interactions, overdoses, and deaths.

The dispensers disclosed herein may be similar to fluid dispensers known as inkjet printheads used in inkjet printing mechanisms, such as printers, plotters, facsimile machines and the like, some of which are described, for example, in Durbeck and Sherr, *Output Hardcopy Devices*, Academic Press Inc., 1987 (ISBN 0-12-225040-0), particularly in chapter 13, pages 311-370. These technologies have in common the extraction of a small quantity of a fluid from a reservoir that is converted into fine droplets and transported through the air to a target medium by appropriate application of physical forces. This technology has been implemented in a variety of ways, but one of the common approaches has been thermal inkjet technology, in which liquids are heated using resistors to form drops and propel them from a chamber through an orifice toward a target. Another approach is piezoelectric inkjet technology, in which movement of a piezoelectric transducer changes a chamber volume to generate the drop.

A typical jet printing mechanism uses cartridges (often called "pens") which shoot drops of liquid colorant (generally referred to as "ink") onto a page. Each cartridge includes a printhead formed with very small nozzles through which the ink drops are fired. Most often, the printhead is held in a carriage which slides back and forth along a guide rod in a reciprocating printhead system, with a target or print media, such as paper, being advanced in steps between each pass of the printhead. To print an image on media, the printhead is scanned back and forth across the page, shooting drops of ink in a desired pattern as it moves. Other printing systems known as "page-wide array" printers, extend the printhead across the entire page in a stationary location and print as the media advances under the printhead. The particular liquid ejection mechanism within either type of printhead may take on a variety of different forms, such as the piezoelectric or thermal printhead technology.

For example, two thermal ink ejection mechanisms are shown in U.S. Pat. Nos. 5,278,584 and 4,683,481, both assigned to the Hewlett-Packard Company. In a thermal system, a barrier layer containing fluid channels and vaporization chambers is located between a nozzle orifice plate and a substrate layer. The substrate layer typically contains linear arrays of heater elements, such as resistors, which are energized to heat ink within the vaporization chambers. Upon heating, an ink droplet is ejected from a nozzle associated with the energized resistor. By selectively energizing the resistors as the printhead moves across the page, the ink is expelled in a pattern on the print media to form a desired image (e.g., picture, chart, or text).

In piezoelectric inkjet technology, an activating pulse is applied to a piezoelectric plate or member attached to a plate, which then responds by flexing to propel an ink drop out of a nozzle. Several examples of piezo-electric inkjet printheads are described in U.S. Pat. Nos. 4,992,808; 6,186,619; and 6,149,968 (assigned to Xaar Technology Ltd.) and U.S. Pat. No. 6,193,343 and WO 00/16981 (assigned to Seiko Epson Corporation).

In a common cartridge configuration, both the fluid reservoir and the printhead are carried by a carriage along the guide rod of the printer. Such printers are known as an "on-axis" printers. Some on-axis printers use "snapper" reservoir systems, in which permanent or semi-permanent printheads are used in conjunction with a detachable reservoir carrying a fresh liquid supply, with the reservoir being snapped into place on the printhead. Another design uses permanent or semi-permanent printheads in what is known in the industry as an "off-axis" printer. In an off-axis system, the printheads carry only a small liquid supply reciprocally back and forth across the printzone, with this on-board supply being replenished through tubing that delivers liquid from an "off-axis main reservoir" placed at a remote, stationary location within or near the printhead. In both the snapper and off-axis systems, rather than purchasing an entire new cartridge which includes a costly new printhead, the consumer buys only a new supply of liquid for the main reservoir or a replacement reservoir already filled with fluid.

In striving to duplicate the quality of photographic film images, the inkjet industry has focused on decreasing the size of ink droplets ejected from the nozzles, as well as accurately placing these droplets on the print media. For instance, some of the more recent inkjet print cartridges are able to deliver droplets about 3-6 picoliters in volume, although larger droplets also may be generated, for example droplets of 10, 50, 100, or more picoliters. The resolution within which currently commercially available inkjet printing mechanisms may place ink droplets on a page is on the order of 1200-2400 dots per inch (known in the industry as a "dpi" rating). Thus, while striving to achieve photographic print quality, inkjet printing technology has become very adept at accurately metering and dispensing fluids. This ability to dispense very small and accurate amounts of fluids (including liquids and powders) is a part of the application systems illustrated herein.

In particular embodiments, the droplet sizes are about 10 $\mu$m or less, such as about 2 $\mu$m to about 8 $\mu$m. In other embodiments, the droplet sizes are greater than 10 $\mu$m, or in some cases greater than 100 $\mu$m. The size of the droplets ejected from a jet dispenser depends in part on the size of the orifice through which the droplets are ejected. In this regard, some printheads include multiple orifices of varying sizes. This allows a single printhead to be used to selectively dispense droplets of different sizes.

In particular embodiments, one or more drop detectors are employed to detect a characteristic of the droplets of fluid dispensed from a jet dispenser. For example, a drop detector may determine whether any droplets are being dispensed from a particular jet dispenser. Other droplet characteristics that can be detected by a drop detector include the volume and velocity of the droplets. The drop detector sends this information to a controller, which can be used to activate an alarm, such as an audio and/or visual alarm, if the detected characteristic does not satisfy a predetermined condition or requirement. In one specific implementation, for example, an alarm is activated if a drop detector determines that a jet dispenser is not dispensing any drops. In another implementation, a controller stops a jet dispenser from dispensing fluid if it is determined that the jet dispenser is not operating within specified parameters. For example, a controller can be used to monitor the dispensing rate of a jet dispenser and stop the ejection of fluid from the jet dispenser if the dispensing rate exceeds a specified dispensing rate. If desired, historical data of the detected characteristics can be stored in memory of a local controller or a remote computing device or computer system. Such data can be used to monitor the past performance of the jet dispensers to determine whether maintenance of the apparatus is required, such as cleaning, repairing, or replacing components. Such data can also be valuable in recording detailed personalized medication records for each patient.

The drop detectors used in the embodiments disclosed herein can be any of various drop detectors known in the art. One type of drop detector is an electrostatic drop detector that charges a drop when the drop is formed. An electrostatic drop detector senses the electric field of the charged drop and produces an output signal in response to the detected drop. An electrostatic drop detector can be used to detect the volume of an ejected drop based upon the amount of electrical charge transferred to an electrostatic sensing element. A similar type of drop detector uses an electrode that, when impacted by a drop, produces a small current to indicate the presence of the drop. Another type of drop detector directs a beam of light at a light sensor (e.g., a photodetector). When a drop passes through the light beam, the output of the light sensor varies accordingly to indicate the detection of the drop. Yet another type of drop detector detects drops that impact a piezoelectric membrane. One such drop detector is disclosed in U.S. Pat. No. 4,835,435 to Yeung et al. U.S. Pat. No. 4,583,975 to Pekkarinen et al., discloses a piezoelectric drop detector mounted to the wall of a chamber. Instead of striking the piezoelectric film directly, the drops strike the surface of accumulated liquid in the chamber and pressure waves travel through the walls of the chamber to the piezoelectric film.

In another representative embodiment, an apparatus for administering a bioactive composition to a subject includes a jet dispenser for dispensing a controlled amount of the bioactive composition in the form of droplets. A fluid manifold is configured to receive the droplets of the bioactive composition dispensed from the jet dispenser. A drop detector detects a characteristic of the droplets dispensed from the jet dispenser. The drop detector can be operatively connected to a controller in a feedback system to provide a warning, such as an audible or visual warning, or to stop the ejection of droplets from a jet dispenser should the drop detector detect a characteristic that does not satisfy a predetermined condition.

In still another representative embodiment, an apparatus for administering a bioactive composition to a subject includes a jet dispenser operable to dispense droplets of the bioactive composition into a fluid chamber. The fluid chamber desirably has a drip surface, a first inlet for receiving an infusion liquid such that the infusion liquid is directed onto the drip surface, a second inlet for receiving the droplets of bioactive composition dispensed from the jet dispenser such that the droplets also are directed onto the drip surface, and a fluid outlet for discharging a mixture of the infusion liquid and the bioactive composition.

In yet another representative embodiment, an apparatus for administering a bioactive composition to a subject includes a plurality of fluid dispensers for dispensing a controlled amount of the bioactive composition and a plurality of fluid chambers for containing and delivering the bioactive composition to the fluid dispensers. The apparatus also includes a fluid manifold having a first inlet for receiving the bioactive composition dispensed from the fluid dispensers, a second inlet for receiving an infusion liquid for mixing with the bioactive composition, and an outlet for discharging a mixture of the infusion liquid and the bioactive composition.

In another representative embodiment, a method for administering a bioactive composition to a subject includes dispensing droplets of the bioactive composition from a plurality of jet dispensers into respective mixing chambers. An infusion liquid is mixed with the bioactive composition in each mixing chamber and a mixture of the infusion liquid and the bioactive composition is discharged from each mixing chamber and infused into a subject. The bioactive composition to be dispensed from each jet dispenser can be the same or different from each other. For example, in one implementation, different bioactive compositions are simultaneously dispensed from the jet dispensers for infusing into the subject.

In another representative embodiment, a method for administering a bioactive composition to a subject includes dispensing from a jet dispenser droplets of the bioactive composition, detecting a characteristic of the droplets dispensed from the jet dispenser, and delivering the bioactive composition to the subject.

More specifically, and referring to FIG. 1, there is shown an infusion system 10, according to one embodiment, for accurately dosing one or more bioactive compositions in infusions. The illustrated system 10 generally includes a dispensing apparatus 12 fluidly connected to one or more fluid containers 14 containing an infusion liquid. The fluid containers 14 can be, for example, flexible bladders, such as plastic bags similar to or identical to the containers which are used to administer intravenous ("IV") fluids to patients in hospitals, ambulances, nursing homes, and the like. The illustrated containers 14 desirably include fixtures, such as eyelets 90, which can be used to hang the containers from a conventional IV stand. In the illustrated system, infusion liquid from the containers 14 is gravity fed into individual fluid chambers (e.g., fluid chambers 22 in FIG. 3) of a fluid manifold 18 (also referred to herein as a mixing unit) via fluid conduits 16, which can be conventional IV tubing. In other embodiments, a single fluid container 14 can be used to supply an infusion liquid to each fluid chamber of the fluid manifold 18.

The dispensing apparatus 12 has multiple fluid reservoirs (e.g., fluid reservoirs 20 in FIG. 3) for containing one or more bioactive compositions, and one or more fluid dispensers (described below) for dosing controlled amounts of bioactive composition from the fluid reservoirs 20 into one or more fluid chambers (also referred to herein as mixing chambers) of the fluid manifold 18. Mixtures of the infusion liquid and the bioactive composition are discharged through fluid conduits 24 that are fluidly connected to the mixing chambers 22. In the illustrated embodiment, the conduits 24 feed the mixtures of the infusion liquid and the bioactive composition to individual pumping units 26. Each pumping unit 26 provides a pressurized flow of fluid to a subject via a respective fluid conduit 28. The pumping units 26 can be conventional infusion pumps. In an alternative implementation, the fluid mixtures can be gravity fed to the subject without the use of the pumping units 26.

As shown in FIG. 1, the system 10 includes a controller 30 for controlling the operation of the dispensing apparatus 12. The controller 30 may be a separate unit electrically connected to the controller 30 with a flexible connector 32, such as shown in FIG. 1. Desirably, the controller 30 is adapted to be mounted or supported by the dispensing apparatus 12. In alternative embodiments, the controller 30 can be integral with the dispensing apparatus 12. The controller 30 and dispensing apparatus 12 receive power either from an onboard battery storage system, which may be located in either the controller 30, the dispensing apparatus 12, or both. Alternatively, power may be supplied from an external source, such a standard electrical outlet. Of course, rechargeable or replaceable batteries may be preferred in some embodiments for ease of portability and use. The controller 30 operates to apply firing signals to the fluid dispensers of the dispensing apparatus 12, which respond by ejecting droplets of fluid from the fluid reservoirs 20 into the fluid chambers 22.

In a simple embodiment, the controller 30 may include an ON/OFF power switch, or button, 34, to which controller 30 responds by beginning and/or ending a fluid ejection sequence. Alternatively, switch 34 may simply serve as an ON switch, with controller 30 determining the precise amount of fluid to be ejected from the fluid dispensers, and then stopping ejection automatically after the selected metered amount has been dispensed. In a more sophisticated embodiment, controller 30 may include an input keypad 36, which can be an alpha or alpha numeric keypad. Using keypad 36, a physician, nurse, pharmacist or other health professional, or the subject to which the fluid will be administered, may input variations in the amount of and types of fluids dispensed. Controller also may include a display screen 38, which can be a liquid crystal display, to indicate which selections have been made using keypad 36 and/or to display different operating parameters of dispensing apparatus 12. Alternatively, keypad 36 may be eliminated, and the controller 30 programmed to display various selections on screen 38. Scrolling buttons 40 and 42 may allow different instructions or selections to be scrolled across, or up and down along, screen 38, including information such as desired dosages, frequency, and potential side effects.

In still other alternative embodiments, the display screen 38 also is a touch screen, in addition to, or in place of, keypad 36. The touch screen may include a series of images that, when touched with a finger or stylus, program the controller 30. Alternatively, the touch screen may include a character recognition area for receiving written inputs using a stylus, such as the graffiti recognition features of the Palm® operating system (Palm, Inc., Santa Clara, Calif.). Thus, a touch screen provides an alternative means for programming the controller in addition to the keypad.

Display screen 38 also may indicate various selections along an upper portion of the screen, adjacent buttons 34, 44, 46 and/or 48, allowing a user to then select a particular drug or dosage by depressing one or more of these buttons. Alternatively, depressing one of the buttons could indicate the occurrence of a particular event, such as an adverse medication response that would alter (for example decrease) a subsequent dosage administration, or an event (such as physical exertion) than can signal a need to alter a medication dosage. The controller also may be programmed to prevent unauthorized alteration of dosages, for example an increase in a dosage of a controlled substance above that authorized by the prescribing physician. Alternatively, the controller can permit certain ranges of dosages to be administered, for example various doses of an opioid pain reliever in response to fluctuating pain. In such situations, information received from other healthcare nodes in the system can enable patient-specific variable on-the-fly updates to dosages while still maintaining safety.

As shown in FIG. 1, a more expedient method of initially programming controller 30, or supplying dosage and other information, may be to use a computer input link 50, selectively attachable to the controller 30, to couple an external computer, microcomputer, or other computing device 52 to controller 30. Other linkage devices may be used to communicate between external computing device 52 and controller 30, such as by using infrared signals, radio waves, modems, wireless networking, direct connections, and the like. For example, a patient can download information stored in the smart device about self-regulated dosage administrations or symptoms experienced (as indicated for example by which buttons have been depressed on the device, and/or the pattern and frequency of the buttons that are pushed). This information can be transmitted over a modem or wireless network to a physician's or other health care provider's office, where it can be displayed (in electronic or other form) to a health care professional, and appropriate action can be taken. For example, if symptoms are noted to be increasing in spite of administration of a therapeutic amount of a particular drug, consideration can be given to providing a new drug or reconsidering the diagnosis for which the drug has been administered. As another example, the controller 30 may include a docking connection for use with a docking station connected to a computer at the physician's office. Thus, connecting the applicator to an external computer provides an alternative means for programming the applicator controller, in addition to the keypad and touch screen mentioned above. In yet another example, the controller can be a smart device in communication with other smart devices coupled to healthcare nodes. In such a system, the controller is effectively a computing device in and of itself and in direct communication with other smart devices coupled to healthcare nodes.

The controller 30 also may be linked to communicate with other devices, such as devices for monitoring the physiological status of a subject. For example, the device may be linked to a blood sugar monitor and programmed to release an anti-diabetic drug if the subject's blood sugar level falls outside the normal range. As another example, the device may be linked to a temperature monitor and programmed to release a fever-reducing (antipyretic) drug if the subject's body temperature rises above a certain threshold. The device may be programmed to automatically release a composition, such as in the case where the device is part of a respiratory mask worn by a bed-ridden patient, or may be programmed to signal the user that a dose of a composition should be administered to the user. The device may also be "smart" and have the ability to automatically determine and generate patient-specific variable drug dosage instructions and subsequently act upon them and/or forward the instructions to a healthcare provider or computer system for safety checks or review.

Alternatively, as shown in FIG. 1, controller 30 may define an input slot 54 which is sized to receive an input device, such as a flash memory card 56 or other removable memory device, which carries input data for controller 30. This removable memory device may be programmed by the controller 30 or some external device, such as a remote computer. For example, the removable memory may be inserted into and programmed by a computer at a physician's office, hospital, clinic, or other health facility and given to the subject for use with the applicator. Indeed, use of the flash memory card 56 or similar memory device in conjunction with controller 30, may result in the only other input device of controller 30 being switch 34. Thus, programmable removable memory provides yet another alternative means for programming the applicator controller, in addition to the keypad, touch screen, and remote computer connection described above. In the embodiment in which the controller is a smart device, memory is integrated within the controller, and information can be transferred wirelessly to update and forward stored information.

In one embodiment, controller 30 may only have an ON switch 34, and be completely preprogrammed via an external computer 52, such as at a doctor's office or pharmacy, prior to giving the device to a patient. In another embodiment, the device may be sold with only an ON switch 34, and with the physician or pharmacy supplying the medication in a kit with a flash memory card 56. In yet another embodiment, the device may only have an ON switch 34, and be completely programmed when in operation within a healthcare system in which one or more other healthcare nodes are in communication via smart devices.

Figure 2:
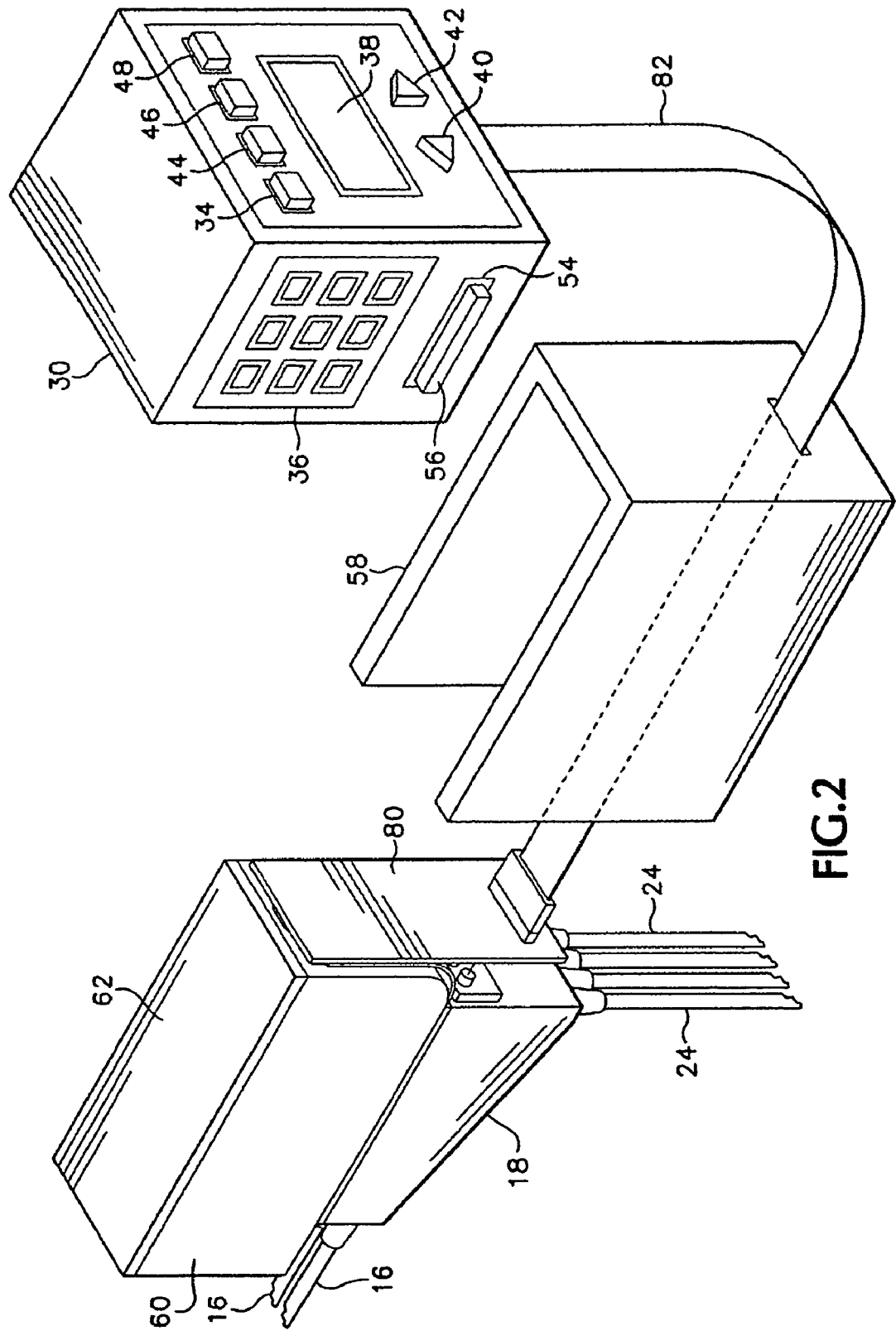
FIG. 2 is a perspective view of a dispensing apparatus, according to one embodiment, for dosing modifications in infusions.
Figure 3:
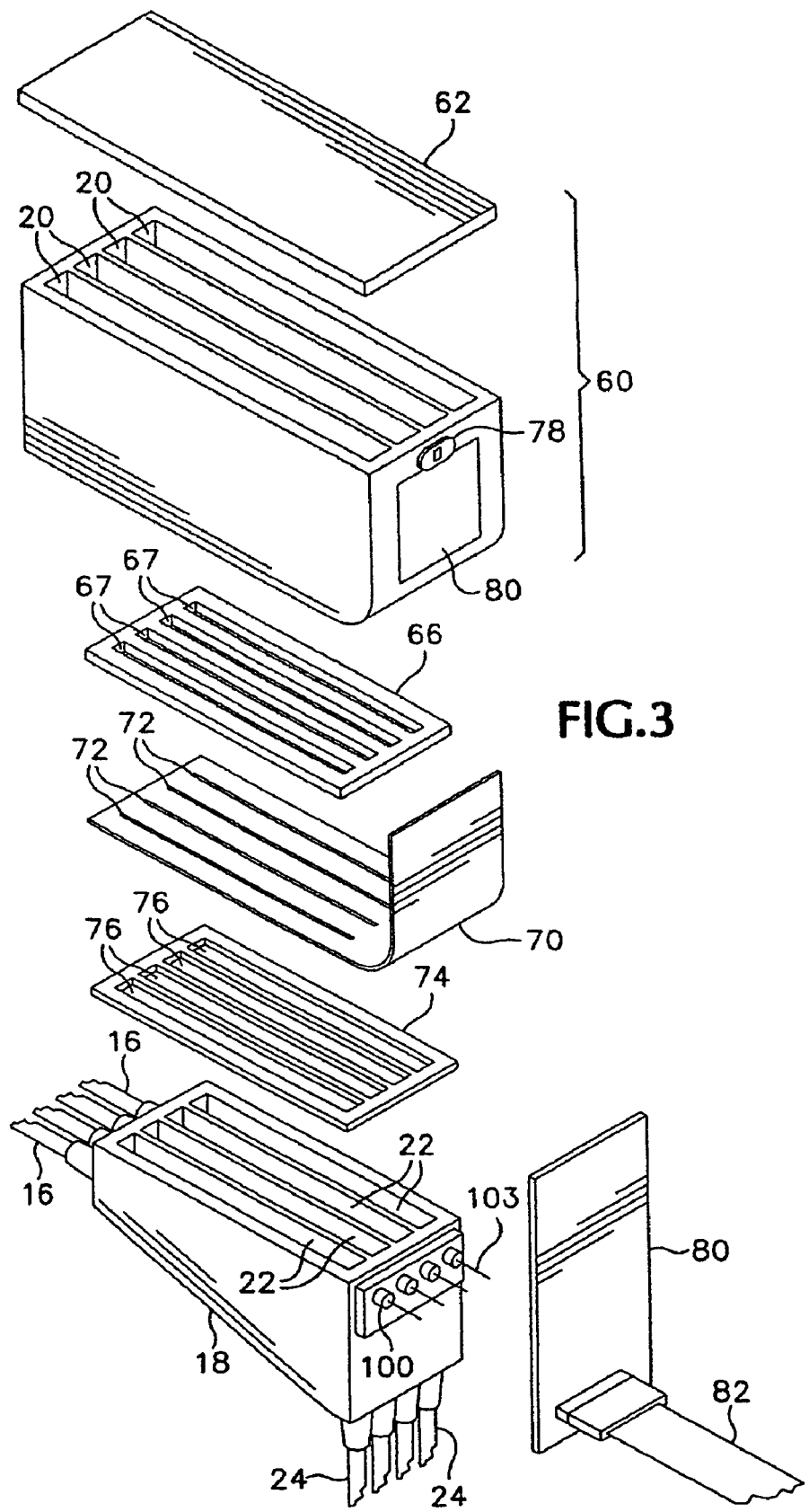
FIG. 3 is a perspective, exploded view of the dispensing apparatus of FIG. 2.
Figure 4:
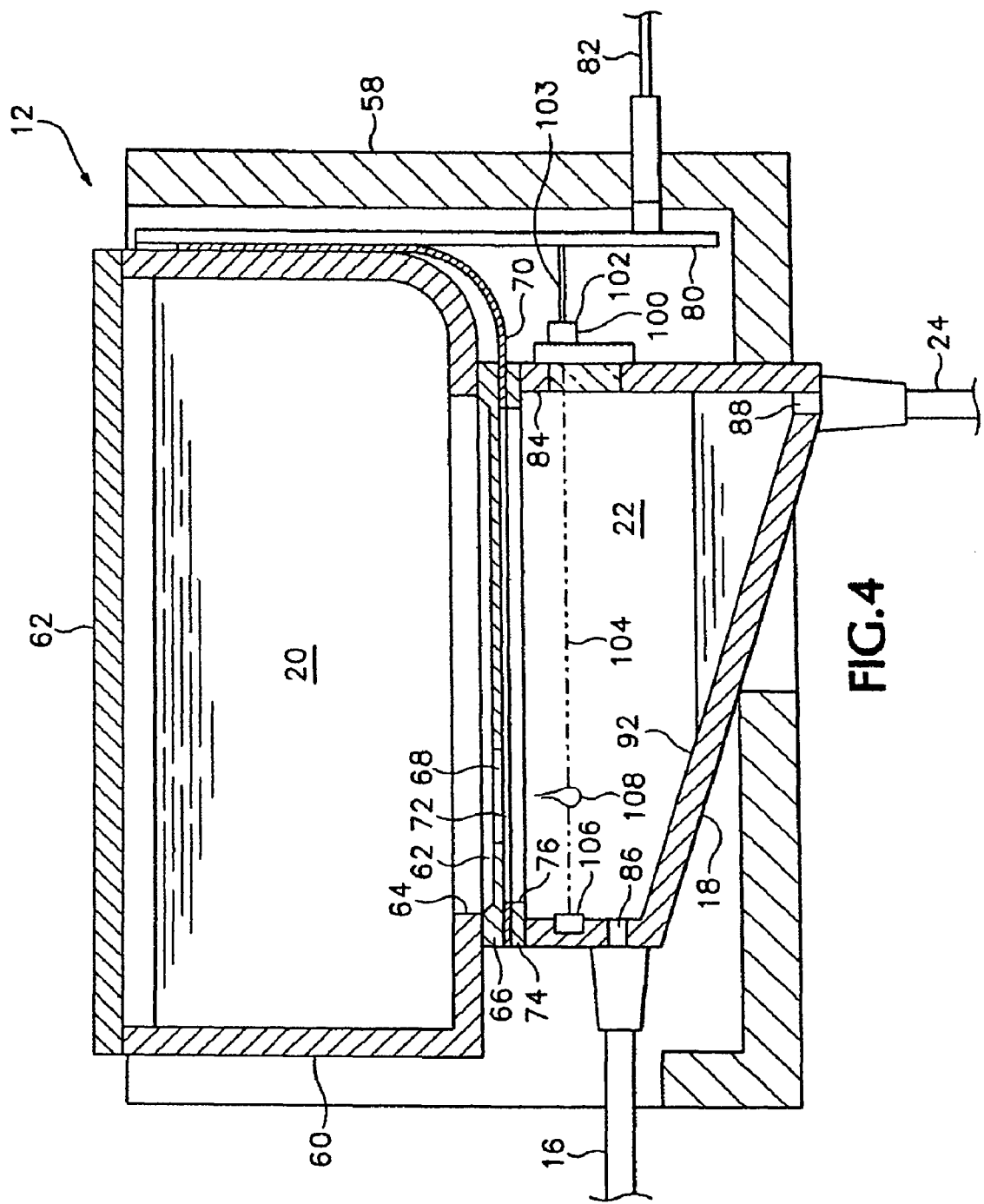
FIG. 4 is a longitudinal cross-sectional view of the dispensing apparatus of FIGS. 2 and 3.

Referring now to FIGS. 2-4, the details of one embodiment of a dispensing apparatus 12 will now be described. As shown in FIG. 2, the illustrated dispensing apparatus 12 includes a removable outer housing 58 for housing the fluid manifold 18 and a fluid reservoir unit 60. The fluid reservoir unit 60 defines a plurality of fluid reservoirs 20 (FIG. 3) for containing bioactive compositions. The fluid reservoir unit 60 also has a removable cover, or lid, 62 for accessing the fluid reservoirs 20 inside the unit 60. In alternative embodiments, the fluid reservoirs 20 may serve as receptacles for receiving replaceable and/or disposable fluid reservoirs (not shown) that contain the bioactive compositions. In such an embodiment, the fluid reservoirs may be removed from their respective receptacles when empty and new fluid reservoirs may be inserted into the fluid reservoir unit 60.

The illustrated housing 58 partially covers the fluid manifold 18 and the fluid reservoir unit 60 and serves as a mounting surface for mounting the controller 30. In another embodiment, the housing 58 completely encloses the fluid manifold 18 and the fluid reservoir unit 60, and is formed with apertures or openings for fluid conduits 16 and 24 and a removable cover for accessing the fluid reservoirs 20. In another embodiment, the controller 30 can be integral with the housing 58.

Figure 5A:
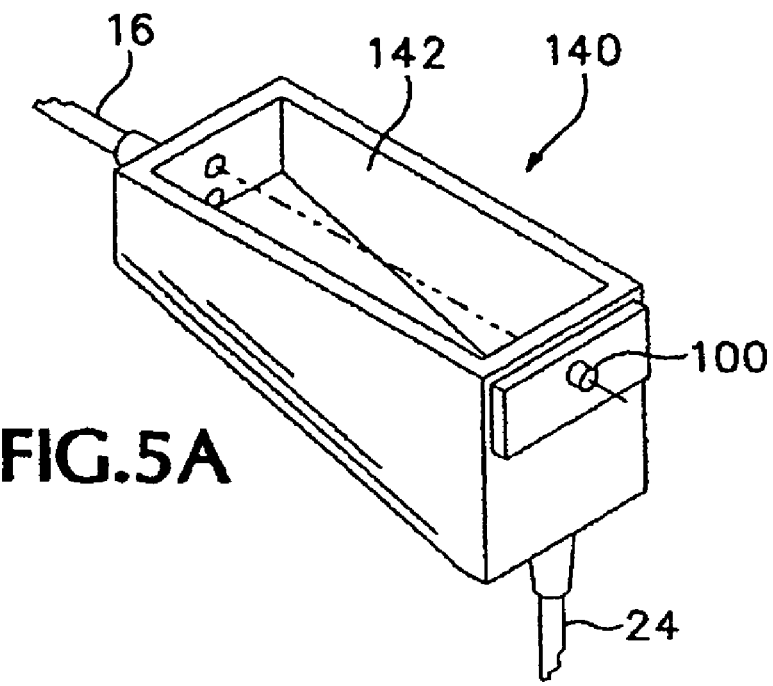
FIG. 5A is a perspective view of an alternative embodiment of a fluid manifold that can be used in the dispensing apparatus of FIGS. 2-4.
Figure 5B:
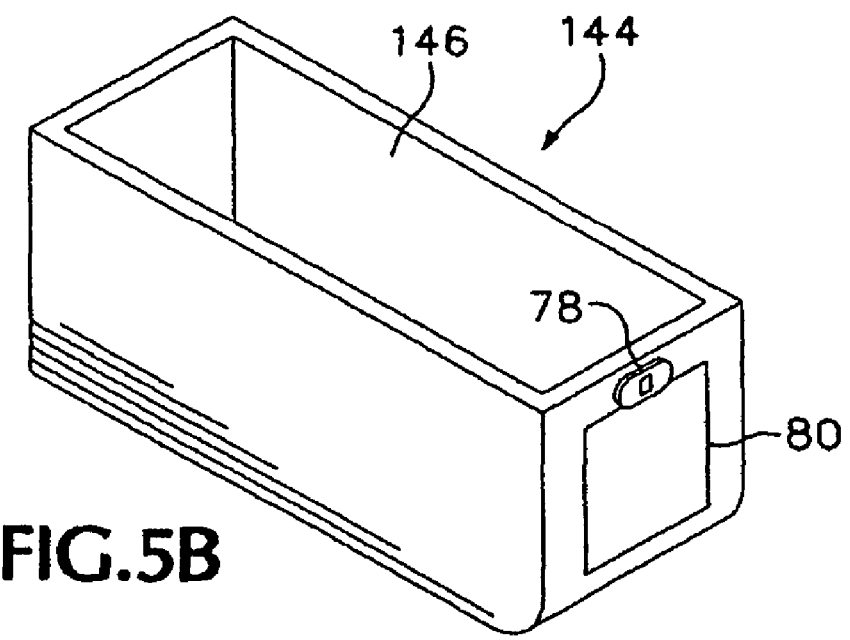
FIG. 5B is a perspective view of an alternative embodiment of a fluid reservoir unit that can be used in the dispensing apparatus of FIGS. 2-4.

As shown in FIG. 4, each fluid reservoir 20 has an outlet opening 64 to allow the bioactive composition to be dispensed into the mixing chambers 22. In the illustrated embodiment, each fluid reservoir 20 is registered with a respective mixing chamber 22 so that fluid from each fluid reservoir 20 will be dispensed into a respective mixing chamber 22. The number of fluid reservoirs 20, however, need not correspond to the number of mixing chambers 22. For example, FIG. 5B shows an alternative embodiment of a fluid reservoir unit 144 that is formed with one fluid reservoir 146 for storing a fluid. The fluid stored in unit 144 can be selectively dispensed into one or more mixing chambers 22 of a fluid manifold 18. In another example, as shown in FIG. 5A, a fluid manifold 140 is formed with one mixing chamber 142, which can be used with fluid reservoir unit 144 or a fluid reservoir unit having multiple fluid reservoirs, such as unit 60.

Interposed between the fluid reservoirs 20 and the mixing chambers 22 are a plurality of fluid dispensers configured to dispense a controlled amount of fluid from the fluid reservoirs 20 into the mixing chambers 22. In particular embodiments, the fluid dispensers are thermal droplet jet dispensers that are operable to heat a volume of fluid to cause the fluid to vaporize and be ejected through an orifice into one of the mixing chambers 22.

As shown in FIG. 3, for example, the illustrated dispensing apparatus 12 includes a substrate 66 (also known as a die) interposed between the reservoir unit 60 and the fluid manifold 18. Substrate 66 is formed with a plurality of generally V-shaped troughs, or channels 67. Each trough 67 is formed with at least one opening, or orifice, 68 (FIG. 4) through which fluid droplets are ejected. The substrate 66 also includes a plurality of individually energizable heater elements (e.g., thin film resistors) (not shown), each being operable to vaporize a volume of fluid, thereby causing the fluid to be ejected through an associated orifice 68, as known in the art. In this manner, each orifice 68 and a respective heater element serves as a thermal jet dispenser for dispensing a controlled amount of fluid. Substrate 66 can be made from any of suitable materials, such as, silicon, glass, or equivalent materials. The construction of substrate 66 can be conventional, such as disclosed in U.S. Pat. No. 5,420,627 to Keefe et al., U.S. Pat. No. 5,278,584 to Keefe et al., or U.S. Pat. No. 4,683,481 to Johnson. In some embodiments, each orifice 68 is of the same size. In other embodiments, the substrate 66 is formed with differently sized orifices 68 for dispensing drops of different sizes.

In the illustrated embodiment, each trough 67 is registered with a respective fluid reservoir 20. In this manner, each fluid reservoir 20 delivers fluid to the orifices 68 of a corresponding trough 67. In alternative embodiments, however, substrate 66 can be configured such that two or more troughs 67 are situated to receive fluid from a single fluid reservoir 20.

A flexible circuit 70 (e.g., a tape automated bond circuit (TAB)) is in electrical contact with conductive traces on the substrate 66 for providing electrical pulses to the heater elements. Circuit 70 can be bonded to the substrate 66 using a suitable adhesive and is formed with a plurality of slots 72 that are aligned with orifices. The construction of circuit 70 can be conventional, such as disclosed in the above-noted patents. A fluid seal 74 having a plurality of openings 76 can be disposed between the circuit 70 and the fluid manifold 18 to prevent, or at least reduce, leakage of fluid and cross-contamination between fluid reservoirs 20. Seal 74 can be made from any suitable materials, such as natural rubber, Teflon®, or various other materials, as known in the art.

In alternative embodiments, other types of jet dispensers can be used. For example, the dispensing apparatus 12 can include a plurality of piezoelectric jet dispensers interposed between the fluid reservoirs 20 and the mixing chambers 22. In other embodiments, fluid dispensers other than jet dispensers can be used for dispensing fluid from the fluid reservoirs 20, although jet dispensers are preferred due to their excellent accuracy and repeatability.

The controller 30 is operatively connected to the heater elements of the substrate 66 to control the firing of fluid from the orifices 68. The illustrated embodiment, for example, includes a printed circuit board 80 mounted to the outside of the fluid reservoir unit 60 and in electrical contact with flexible circuit 70 (FIGS. 2-4). The printed circuit board 80 is electrically connected to the controller 30 via a flexible ribbon connector 82 to complete the electrical connection between the controller and the substrate. Other electrical components can be implemented to permit the controller 30 to control the operation of the jet dispensers via a hardwired connection or a wireless connection.

As best shown in FIG. 4, each mixing chamber 22 has a first fluid inlet 84 aligned with the orifices 68 of a respective trough 67 to receive fluid dispensed therefrom, a second fluid inlet 86 to receive an infusion liquid from a respective fluid conduit 16, and a fluid outlet 88 in communication with a respective fluid conduit 24. As can be appreciated from FIG. 4, droplets of bioactive composition dispensed into a mixing chamber 22 mixes with the infusion liquid in the mixing chamber and a mixture of the infusion liquid and the bioactive composition flow outwardly through outlet 88 into a respective fluid conduit 24.

The manifold 18 desirably, although not necessarily, has a bottom surface 92 that is sloped to direct the accumulated fluid to the outlet 88 (as best shown in FIG. 4). The inlet 86 desirably is positioned at the higher end of the chamber 22 so that the infusion liquid entering the chamber 22 flows over the bottom surface 92 before accumulating at the lower end of the chamber 22. Also, the orifices 68 desirably are positioned such that the ejected droplets 108 impinge the bottom surface 92 before mixing with the accumulated fluid in the chamber 22. In this manner, the bottom surface 92 serves as a "drip" surface for the droplets 108 ejected from orifices 68. By directing the droplets 108 of the bioactive composition onto the bottom surface 92, the incoming infusion liquid flows over the bioactive composition to facilitate dispersion of the bioactive composition in the infusion liquid.

In certain embodiments, the fluid manifold 18 and the fluid reservoir unit 60 are configured to be connectable to and detachable from each other and various fluid manifold and fluid reservoir unit configurations are provided to allow a user to select a specific fluid manifold and fluid reservoir unit configuration for a particular application. For example, when dispensing only one type of bioactive composition, either a reservoir unit having multiple reservoirs (FIG. 3) or a reservoir unit having a single reservoir (FIG. 5B) can be used with a single-chambered fluid manifold (FIG. 5A). In another example, when different bioactive compositions can be mixed together in the same infusion liquid, a single-chambered fluid manifold (FIG. 5A) can be used in lieu of a multi-chambered fluid manifold (FIG. 3).

In one implementation of the dispensing apparatus 12, each fluid reservoir 20 contains a different bioactive composition and the dispensing apparatus 12 is used to simultaneously dose the different bioactive compositions into the mixing chambers 22 at specified dispensing rates. As used herein, the term "dispensing rate" refers to the volumetric flow rate of fluid from a jet dispenser. A user or health care professional can input the prescribed dosage for each bioactive composition into the controller 30, which then controls the firing frequency of each jet dispenser to accurately dose the bioactive compositions into the infusion liquid. In another implementation, each fluid reservoir may carry the same bioactive composition, with the controller 30 dispensing fluid from one fluid reservoir 20 until empty, followed by another fluid reservoir 20, and so forth.

In particular embodiments, the dispensing apparatus 12 has a memory chip, such a programmable memory chip or a flash chip, that contains data relating to certain operating parameters of the jet dispensers. In particular embodiments, for example, the memory of the memory chip contains the average size (i.e., volume) and/or weight of fluid droplets that are dispensed from each orifice 68. In use, a user inputs into the controller 30 the treatment parameters, including the amount of bioactive composition to be administered to the subject, and if desired, the time period over which it is to be administered. The controller 30 is programmed to access this data and calculate the firing frequency required to accurately deliver the prescribed dosage of a bioactive composition to the subject over the specified time period. The controller 30 also can be used in cooperation with one or more drop detectors (e.g., drop detector 100, described below) in a feed-back loop to ensure proper operation of the dispensing apparatus 12, as further described below.

In the illustrated configuration, a memory chip 78 is mounted to the outside of the fluid reservoir unit 60 and is in electrical contact with flexible circuit 70 via another flexible circuit 80. In another embodiment, the memory chip 78 can be physically mounted to a circuit board inside the controller 30. Alternatively, the information stored in the memory chip 78 can be stored directly in the memory of the controller 30 or on flash memory card 56, in which case a separate memory chip would not be required. In still other embodiments, a smart card can be used in the alternative of using multiple memory and controlling devices and chips.

To determine whether any jet dispensers are operating in an improper manner, e.g., an orifice 68 is clogged and not dispensing fluid, fluid sensors, such as the illustrated optical drop detectors 100, are positioned below the orifices 68. As best shown in FIG. 4, each drop detector 100 includes a light emitter 102 operable to emit a beam of light 104 through a respective mixing chamber 22 and a light sensor 106 positioned opposite the light emitter 102 to detect the light beam 104. Each light emitter 102 is connected to the circuit board 80 via a conductor 103. The light beam 104 intersects the ejection path of drops 108 dispensed from orifice 68 such that when a fluid drop 108 travels through the light beam 104, the light sensor 106 sends a signal to the controller 30 indicating the presence of the drop 108. If the drop detector does not detect that a drop has been ejected from the orifice 68, the controller 30 activates an alarm, or other warning device, to warn the subject and/or health care professional monitoring the subject. The alarm can be an audio alarm operable to provide an audible signal, such as a beeping sound or a buzzer, and/or a visual alarm, such as one or more indicator lights mounted in a convenient position on the dispensing apparatus 12. The alarm also may take the form of a written warning displayed on the display screen 38. Alternatively, the alarm can provide a tactile signal, such as a vibratory or vibrating signal similar to those used on pager devices.

In another implementation, the controller 30 calculates the actual frequency at which drops are being ejected from each orifice 68 based on signals from the drop detectors 100 and compares the actual frequency to the pre-set firing frequency of each orifice 68 to ensure that the prescribed dosage is being administered to the subject at the proper rate. If a jet dispenser is dispensing fluid faster or slower than the required rate, then the controller 30 activates the alarm, displays a warning on the display screen 38, and/or controls the jet dispenser to immediately stop dispensing fluid.

Drop detectors other than the illustrated optical drop detectors also can be implemented in the dispensing apparatus. For example, piezoelectric elements can be mounted to the inside surfaces of mixing chambers 22 to detect drops impinging the piezoelectric elements or the fluid in the mixing chambers, such as disclosed in U.S. Pat. No. 4,583,975 discussed above. In another example, an electrostatic drop detector may be used to detect the firing frequency as well as the volume of drops that are ejected from the jet dispensers. The controller 30 then calculates the dispensing rate of each jet dispenser and initiates a particular protocol (e.g., activating an alarm and/or stopping a jet dispenser from ejecting drops) if the dispensing rate is greater or less than the required rate.

In another application of the dispensing apparatus 12, one or more bioactive compositions can be dosed into the fluid manifold 18 and then administered to a subject without being diluted in an infusion liquid. Of course, in such an application, the fluid manifold 18 would not require fluid inlets 86 for receiving the infusion liquids.

Figure 6:
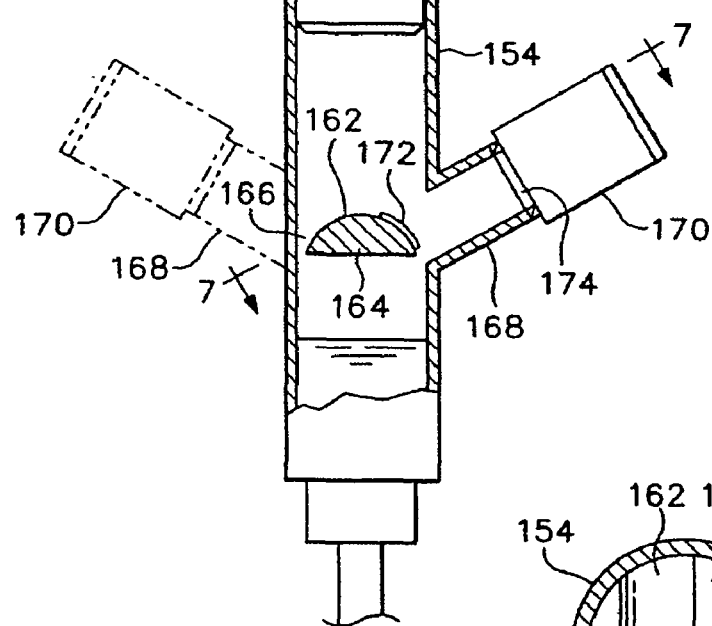
FIG. 6 is an elevational view of another embodiment of an infusion system, having a dispensing apparatus and a drip chamber, with the drip chamber shown partially in section.
Figure 7:
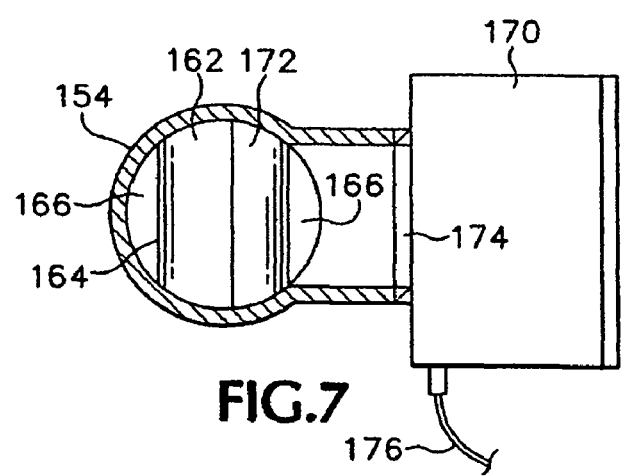
FIG. 7 is an enlarged view of the drip chamber and dispensing apparatus of FIG. 7 taken along line 7-7 of FIG. 6.

FIGS. 6 and 7 illustrate another infusion system, indicated generally at 150, for administering a bioactive composition to a subject. The illustrated system 150 includes a fluid container 152 for containing an infusion liquid and a drip chamber 154 (which serves as the fluid manifold in this embodiment) for receiving the infusion liquid. The drip chamber 154 may include an upwardly extending spike 156 used to puncture the outlet portion 158 of the fluid container 152, as generally known in the art. The spike 156 has an internal passageway that directs fluid from the container 152 to flow into a drop former 160 configured to produce drops of fluid that fall into the drip chamber 154. The construction of drop former 160 can be conventional. In particular embodiments, for example, the drop former includes a narrow fluid conduit (not shown) that produces drops due to the surface tension of the fluid flowing through the conduit. The drop former 160 can be integral with the spike 156 as shown in FIG. 6, or alternatively, the drop former and the spike can be separately formed, interconnecting components.

The drip chamber 154 desirably includes a drip surface 162 positioned underneath the outlet of the drop former 160 such that drops of the infusion liquid fall from the drop former onto the drip surface 162 before accumulating in the bottom portion of the drip chamber 154. The illustrated drip surface 162 is the convex upper surface of a rib 164 extending radially across the inside of the drip chamber 154. Openings 166 are defined between the sides of rib 164 and the inside surface of the drip chamber 154 to allow fluid to flow off of the drip surface 162 and accumulate at the bottom of the drip chamber 154.

The drip chamber 154 also includes a fluid inlet conduit 168. Mounted to the end of the inlet conduit 168 is a dispensing apparatus 170 for dosing one or more bioactive compositions into the drip chamber 154. The drip chamber 154 can include an additional inlet conduit 168, with an additional dispensing apparatus 170, as shown in phantom in FIG. 6. The construction of dispensing apparatus 170 is similar to the construction of the dispensing apparatus 12 shown in FIGS. 2-4. One difference between apparatus 12 of FIGS. 2-4 and apparatus 170 of FIGS. 6 and 7 is that the latter does not include a fluid manifold 18. In lieu of fluid manifold 18, droplets of bioactive composition are dispensed from one or more fluid reservoirs of dispensing apparatus 170 into the drip chamber 154 for mixing with the infusion liquid. A gasket 174 can be interposed between the opening of the fluid conduit and apparatus 170 to provide a fluid-tight seal therebetween. As in the previous embodiments disclosed herein, a controller (e.g., a controller 30) can be used to control the operation of the apparatus 170. The controller can be mounted to the apparatus or remotely mounted and connected via a link 176 (FIG. 7).

The system 150 also may include a drop detector for detecting the presence of drops ejected from the dispensing apparatus 170 and/or for detecting various other characteristics of the drops that are ejected from the dispensing apparatus 170. In the illustrated embodiment, a piezoelectric element 172 of a piezoelectric detector can be mounted on the drip surface 162 for detecting drops dispensed from the dispensing apparatus 170. In other embodiments, an electrostatic drop detector, or an optical drop detector, such as a drop detector 100 (FIGS. 3 and 4), can be used.

As shown in FIG. 6, the dispensing apparatus 170 desirably is positioned such that ejected drops impinge the piezoelectric element 172, or alternatively, the drip surface 162 itself if the piezoelectric element 172 is not provided. This allows the infusion liquid to mix with the bioactive composition as it flows over the drip surface 162 to facilitate dispersion of the bioactive composition in the infusion liquid.

Figure 8:
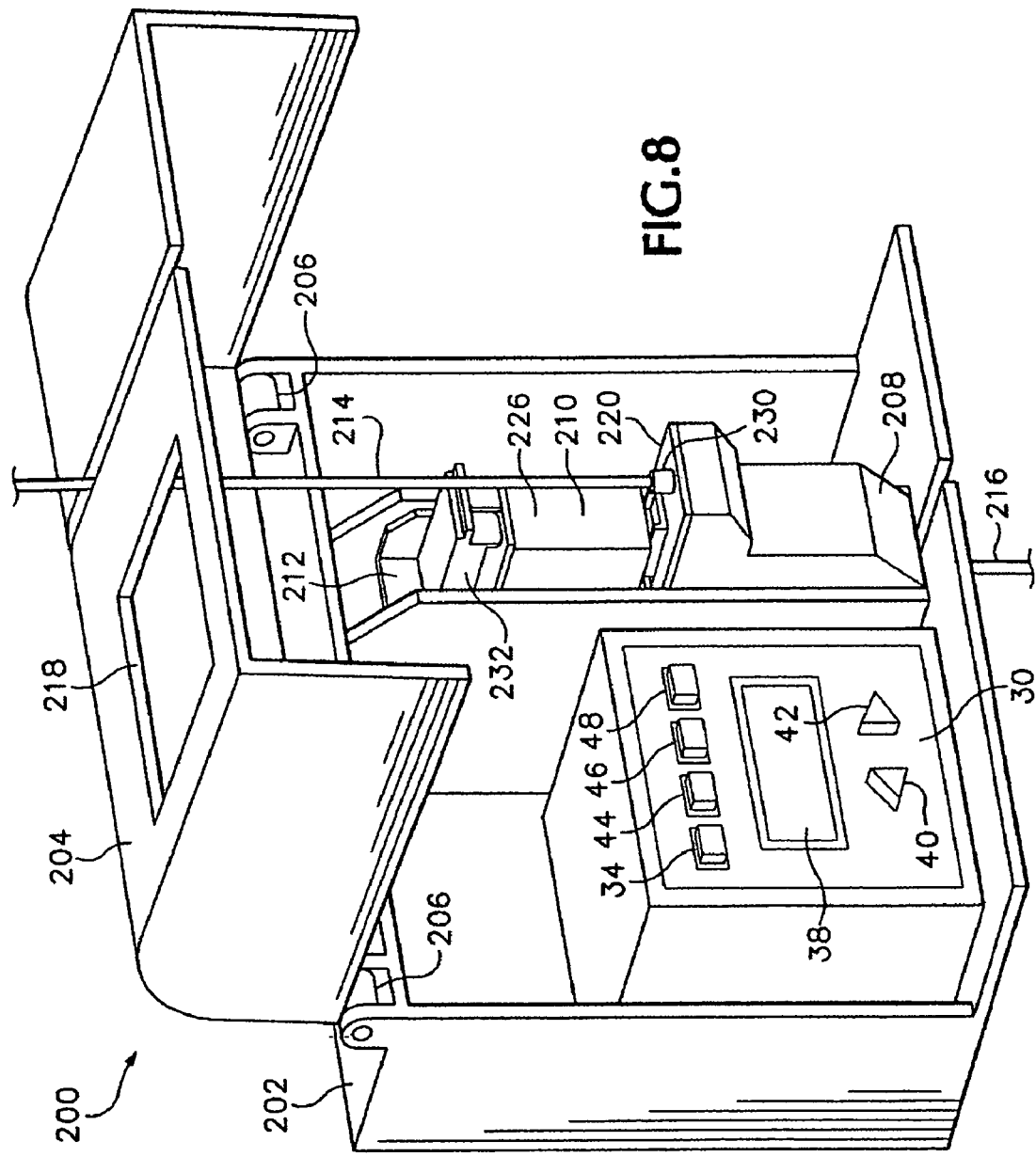
FIG. 8 is a perspective view of another embodiment of an infusion system.
Figure 9:
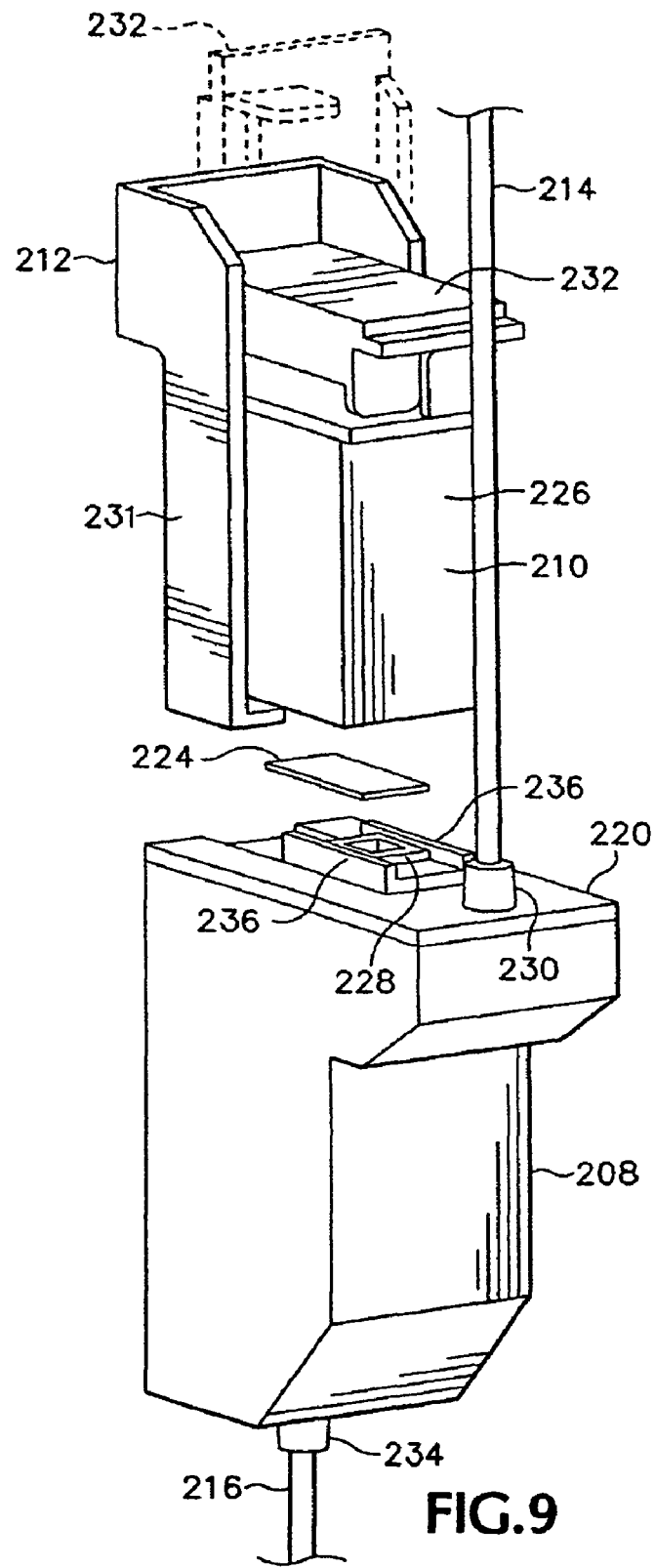
FIG. 9 is a perspective, exploded view of the dispenser, dispenser holder, and fluid manifold of the system of FIG. 8.

FIGS. 8 and 9 illustrate another infusion system, indicated generally at 200, for administering a bioactive composition to a subject. As shown in FIG. 8, the illustrated system 200 includes a main housing 202 and a door 204 mounted at hinges 206. The door 204 is swingable between a closed position and an open position (as shown in FIG. 8) to access the components inside the housing 202. Mounted inside the housing 202 is a controller 30, a fluid manifold 208, a dispenser 210 for dispensing droplets of bioactive composition into the fluid manifold 208, and a dispenser support 212. The door 204 can include an opening 218 to allow a user to access the controller 30 without opening the door 204. A fluid conduit 214 delivers an infusion liquid from a fluid container (not shown in FIGS. 8 and 9) to the fluid manifold 208. An outlet fluid conduit 216 delivers a solution of the infusion liquid and a bioactive composition to a subject or to a pump for pumping the solution into the subject.

As shown in FIG. 9, the fluid manifold 208 in the illustrated configuration includes a cover, or lid, 220 that also serves as an interface between the fluid manifold 208 and the dispenser 210. The cover 220 is formed with a first fluid inlet (not shown) positioned between ribs 236 and dimensioned to receive drops of fluid ejected from the dispenser 210. The cover 220 also is formed with a second fluid inlet 230 for receiving the infusion liquid from fluid conduit 214 and a fluid outlet 234 for discharging solution to the outlet fluid conduit 216.

In the illustrated embodiment, the dispenser 210 includes a reservoir portion 226 for containing fluid and a thermal inkjet substrate 224 formed with a plurality of ejection orifices (not shown) and corresponding heater elements (not shown) (e.g., resistors). When assembled, the substrate 224 is positioned between the ribs 236 to align the orifices over the first fluid inlet in the cover 220. A gasket, or seal, 228 desirably surrounds the first fluid inlet to provide a fluid-tight seal between the fluid manifold 208 and the dispenser 210.

The illustrated dispenser support 212 includes a main body 231 and latch 232 hingedly connected to the main body 231 for releasably securing the dispenser 210. The latch 232 is pivotable between a latched position (as shown in FIG. 9) engaging the dispenser 210 and an unlatched position (as shown in phantom in FIG. 9) to allow removal and replacement of the dispenser 210.

In the particular embodiments, the dispenser 210 is a conventional inkjet cartridge (also known as a pen), and the dispenser support 212 is a conventional printer carriage configured to receive the cartridge. The construction of dispenser 210 can be modified from a conventional inkjet construction to accommodate, for example, the characteristics of the particular fluid to be dispensed. The cartridge can be a single-chamber cartridge, or alternatively, a multi-chamber cartridge that can be used to dispense more than one type of bioactive composition. In addition, the cartridge can have an "on-axis" configuration or an "off-axis" configuration, as discussed above. For example, the dispenser 210 and support 212 can be any of various commercially available thermal or piezoelectric cartridges and carriages, such as any of the 500, 700, 800, and 900 series TIJ (thermal inkjet) carriage and pen assemblies, available from Hewlett-Packard Company for use in inkjet printers.

Many other variations of devices are within the scope of this disclosure. For example, an optical sensor can be incorporated into the controller 30 to read patient identification, such as a bar code on a patient's hospital identification bracelet, with this information being used by the controller to adjust the dosage and/or type of medication administered.

Figure 10:
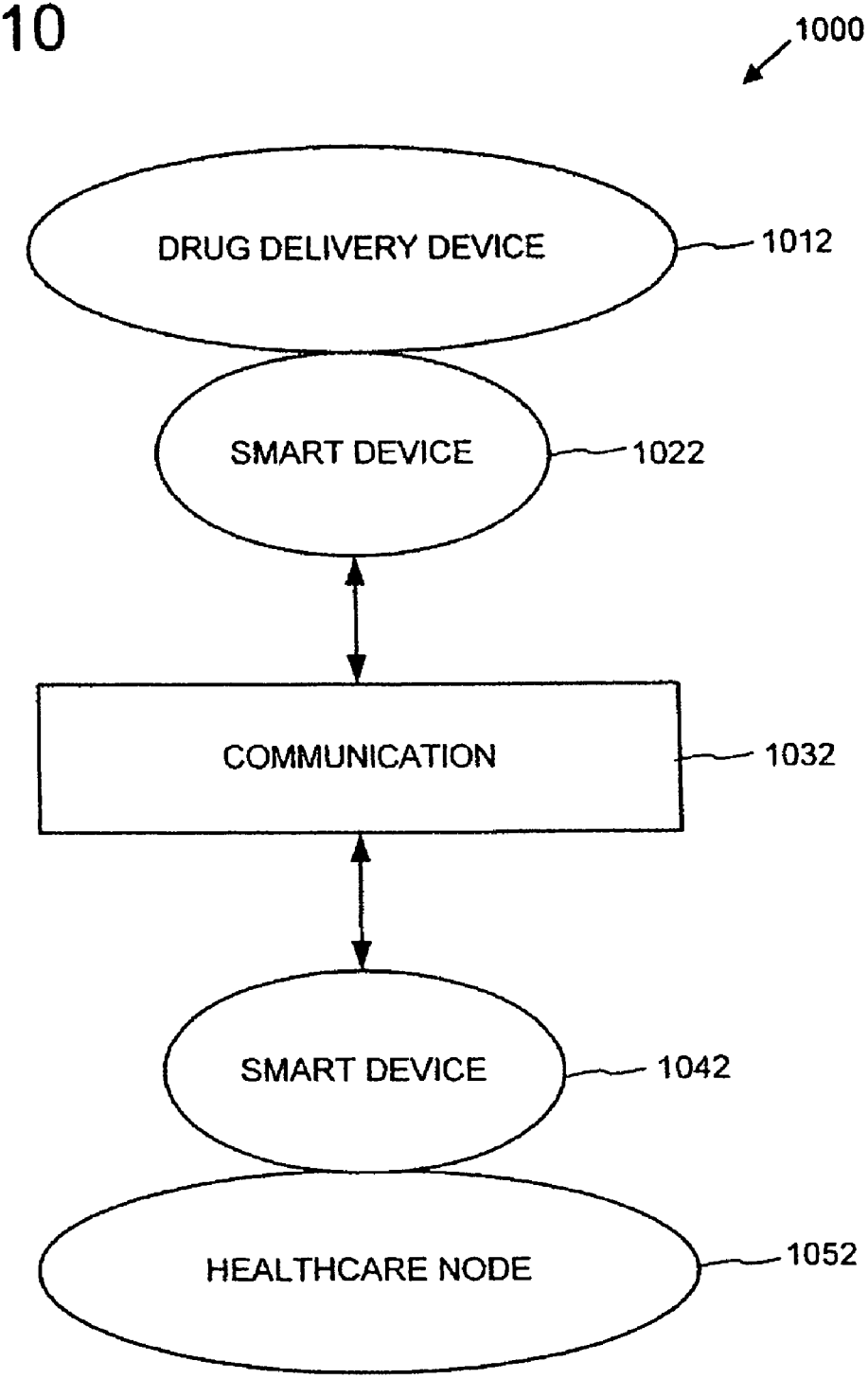
FIG. 10 is a block diagram of an exemplary system for administering a bioactive composition to a subject.

FIG. 10 shows an exemplary system 1000 for administering a bioactive composition to a subject, according to one embodiment. Infusion systems shown in FIGS. 1-9 and described above can be implemented in system 1000. Additionally, other drug delivery devices can be implemented in system 1000. For example an inhaler having jet dispensers as described in U.S. Pat. No. 6,684,880, and/or a cutaneous drug delivery system having jet dispensers as described in U.S. Pat. No. 6,723,077, both of which are hereby incorporated by reference, can be implemented in system 1000.

The system 1000 includes a drug delivery device 1012 that is coupled to a smart device 1022 (which can be, for example, the controller 30 of FIG. 1) and is in communication as indicated at 1032 with a smart device 1042 coupled to a healthcare node 1052. As used herein, a smart device coupled to a healthcare node means that a smart device can be attached to, worn by, or embedded within (for example, a smart device can be implanted into a patient or medical professional) a healthcare node. Any combination of the technologies described herein, including wireless networking, infrared, and the like can be used for communicating information between the smart device 1022 and the smart device 1042. Furthermore, a smart device can be linked to a healthcare node via a wireless connection as described above.

In any of the examples described herein, a variety of information can be determined from the communication 1032 for administration of the bioactive composition. For example, personalized and variable administration instructions can be determined for a patient based on the information communicated between the healthcare node 1052 and the drug delivery device 1012 via the respective smart devices 1042 and 1022. Although the illustrated system shows one healthcare node and a corresponding smart device, multiple healthcare nodes having respective smart devices can be utilized in the system.

Methods for administrating a bioactive composition to a subject are described in detail below.

Figure 11:
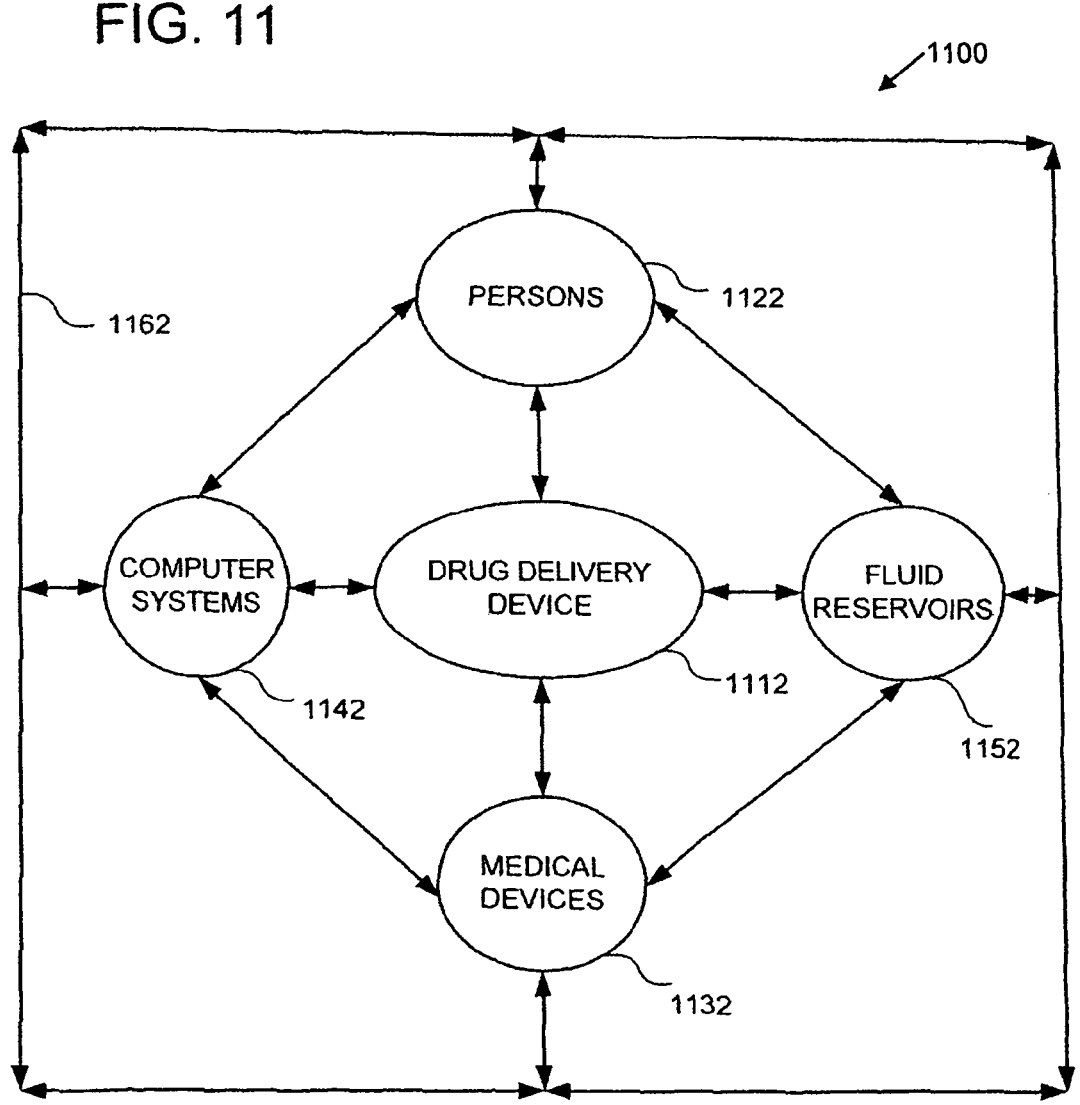
FIG. 11 is a block diagram of an exemplary system for administering a bioactive composition to a subject via communication between healthcare nodes.

FIG. 11 shows an exemplary system 1100 for administering a bioactive composition with a drug delivery device 1112 that is in communication with multiple healthcare nodes, including persons 1122, computer systems 1142, fluid reservoirs 1152, and medical devices 1132. Each node can have a respective smart device (not shown in FIG. 11) to facilitate the transfer of information within the system. Infusion systems shown in FIGS. 1-9 and described above can be implemented in system 1100. Additionally, other drug delivery devices can be implemented in system 1000, such as described above.

The drug delivery device 1112 can be in communication with the other healthcare nodes via an IT (information technology) infrastructure 1162 and the smart devices coupled to respective healthcare nodes.

Persons 1122 can include, for example, patients, doctors, nurses, medical support staff, pharmacists, lab technicians and the like. Information that can be communicated from human subjects includes, but is not limited to, identification data. Medical devices 1132 can include, for example, devices that register a patient's vital signs (i.e. body temperature, pulse rate, respiration rate, blood pressure and the like) such as aneroid monitors, digital monitors, medical telemetry devices, respirators, thermometers, and the like. Computer systems 1142 can include, for example, software systems such as electronic medical record systems, decision support systems, medical payment provider systems, as well as general all-purpose computer systems, such as large servers and networked personal computers in which computerized support system data resides. Furthermore, computer systems can include personal digital assistants, handheld computers, tablet computers and the like. Computerized support system data includes, but is not limited to, payment provider information, patient medical information, and decision support information.

Finally, fluid reservoirs 1152 can be any container, cartridge, or similar device that contains a bioactive composition that is to be administered to a patient by the drug delivery device 1112. For example, the fluid reservoirs 1152 can be the fluid reservoirs 20 of FIG. 3 or drug cartridges that are removable from the drug delivery device. Such removable drug cartridges can be re-usable or disposable.

The information transferred between healthcare nodes can be stored on the computer system 1142 to create an extensive health history for patients that can be used by health professionals to diagnose or treat a patient.

Bioactive composition data can be communicated between all healthcare nodes and reside in various nodes (more specifically stored on the smart cards associated with the nodes). The communication can be two-way or one-way between health care nodes. Bioactive composition data can include, but is not limited to, fluid reservoir data (e.g. the type and quantity of drug in the fluid reservoir), stored and/or measured data (e.g. dosage amount, dosage rate (for example, dispensing rate, dosage flow rate, such as cc/min., or the like), dosage frequency (for example, how many times per day a dose is administered or dispensed), dosage ratio (for example, the ratio of one drug to another drug or the ratio of a drug to a saline solution mix), safety data, expiration date, and expiration time) and any prescription data (e.g. the prescribed bioactive composition, the prescribed dosage amount, the prescribed dosage rate, the prescribed dosage frequency, and the identification data of the patient for which the bioactive composition is prescribed). Prescription data can be compared with measured (and/or stored) data as a safety measure.

Such communication can purposely produce redundancy, automated and manual checks and balances and the capability of closing the loop with drug delivery, vital signs data, and medical history information. Such feedback control loops can ensure that the right patient gets the right drug through the right route at the right dosage and time.

Figure 12:
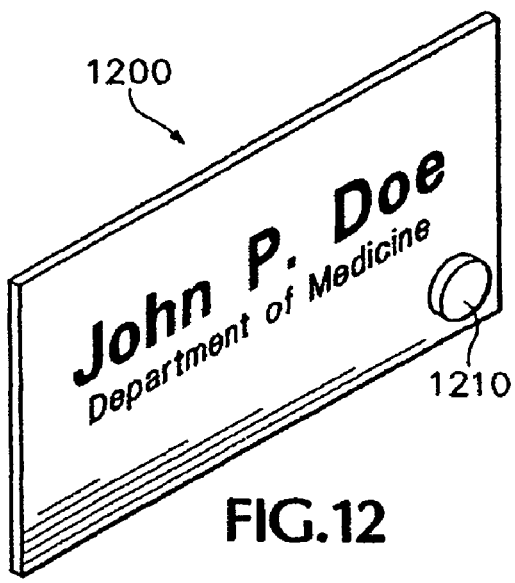
FIG. 12 is a perspective view of a wearable badge for mounting a smart device to a human subject, according to one embodiment.
Figure 13:
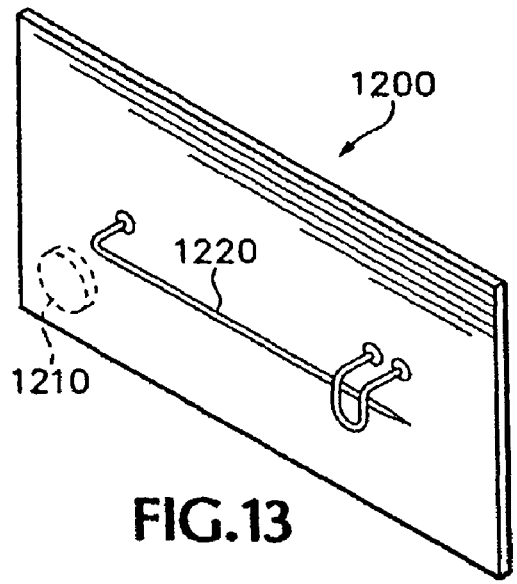
FIG. 13 is a perspective view illustrating the back of the badge shown in FIG. 12.

FIGS. 12 and 13 illustrate a wearable smart device that can be worn by a person, according to one embodiment. The smart device enables communication with a smart device-enabled healthcare system. The illustrated embodiment comprises an identification badge 1200 that mounts a smart device 1210 for communicating, storing, and processing information. The badge 1200 can include a pin 1220 or other suitable mechanism for mounting the badge on the clothing of a person. Commonly, the badge 1200 would be worn by medical staff and professionals and related business people. However, depending on the systems and methods in practice in a healthcare system, a wearable smart device such as that illustrated could also be worn by patients.

Figure 14:
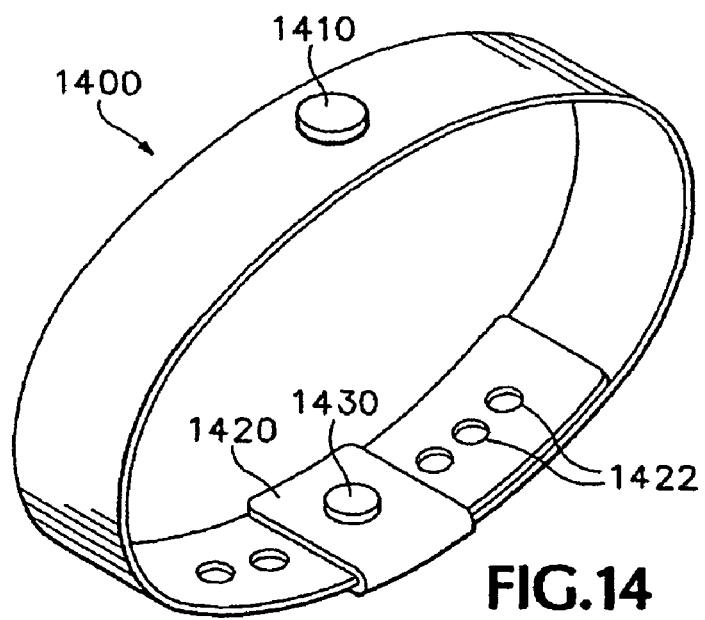
FIG. 14 is a perspective view illustrating an armband adapted to be worn by a human subject and upon which a smart device can be mounted, according to one embodiment.

FIG. 14 illustrates a smart device that can be worn on the arm, wrist, or ankle of a person. The smart device enables communication with a smart device-enabled healthcare system. The illustrated embodiment comprises a band 1400 (which can be made from plastic, fabric, paper, or other suitable materials), such as those commonly given to a patient upon check in at a hospital, and a smart device 1410 mounted to the band for communicating, storing, and processing information. The band can include a plurality of apertures 1422 on one end portion, while the other end portion can include a post 1430 and foldable flap 1420 which is also formed with an aperture. The band can be secured to the patient's wrist, arm, or ankle by wrapping the band around the body part and inserting the post 1430 through a selected aperture 1422 and folding flap 1420 over the post 1430. The post 1430 can be formed with an enlarged end portion having a diameter that is greater than that of the aperture in the flap 1420 to the secure the flap in its folded position. A clip or snap also can be used to secure the band. While the band is commonly used for patients, it is not limited to patients and can be worn by other persons, such as doctors, nurses, pharmacists, laboratory technicians, and the like.

Figure 15:
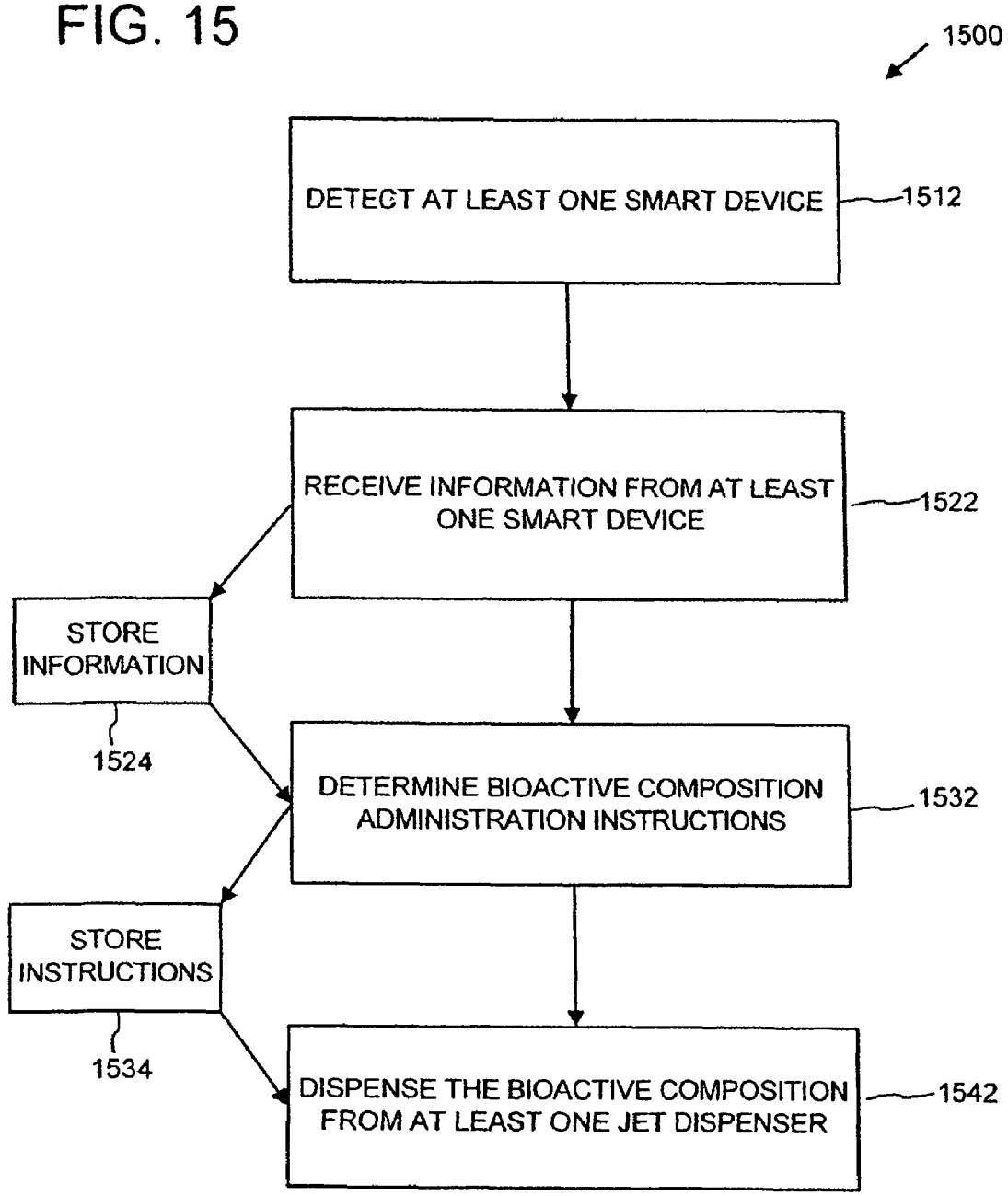
FIG. 15 is a flowchart showing an exemplary method for administering a bioactive composition to a subject.

FIG. 15 shows an exemplary method 1500 for administering a bioactive composition to a subject, according to one embodiment. The method 1500 can be performed, for example, by the system 1000 of FIG. 10 or the system 1100 of FIG. 11.

At 1512, at least one smart device coupled to a healthcare node is detected by another smart device coupled to a drug delivery device having at least one jet dispenser. Detection can be achieved via wireless networking, infrared, radio waves, or any other form of communication. Proximity devices (for example, devices that can detect smart devices within a certain proximity and can be operable to forward information between smart devices, thereby increasing communication range between smart devices coupled to healthcare nodes) mounted on or coupled to walls or other areas within a healthcare system can also be used in coordination with the smart device coupled to the drug delivery device to detect other healthcare nodes.

At 1522, information is received from the detected smart device.

At 1524, the received information is stored. It can be stored on the smart device coupled to the drug delivery device or forwarded to another computer system and/or smart device for storage. The stored information can be used to create a health history for the patient.

At 1532, instructions for administering the bioactive composition are determined based on the information received and any other available information. For example, the information received can be analyzed by comparing the various information in order to create administration instructions that can then be communicated to the drug delivery device. Comparing can include but is not limited to comparing bioactive composition data, human subject data, computerized support system data and medical device data with each other to enable matching of patients with proper medication, safety checks and balances, and patient-specific variable rate customized drug administration. As will be shown in detail below, such comparing of data transferred between smart healthcare nodes can automate the drug delivery administration process so that the drug can be infused according to an optimized curve for the patient (i.e. patient-specific variable drug delivery or personalized drug distribution). In such a system, adjustments also can be made manually by health professionals and possibly the patients themselves.

At 1534, the administration instructions that are determined are stored. They can be stored on the smart device coupled to the drug delivery device or forwarded to another computer system and/or smart device for storage. The stored administration instructions can be valuable as they further augment the health history data for the patient. In addition to being stored in the health history file of the patient, the administration instructions can also be saved as a separate file which details the instructions over time. This further providing checks and balances within the system.

At 1542, the drug delivery device dispenses the bioactive composition from the at least one jet dispenser based on the administration instructions.

Figure 16:
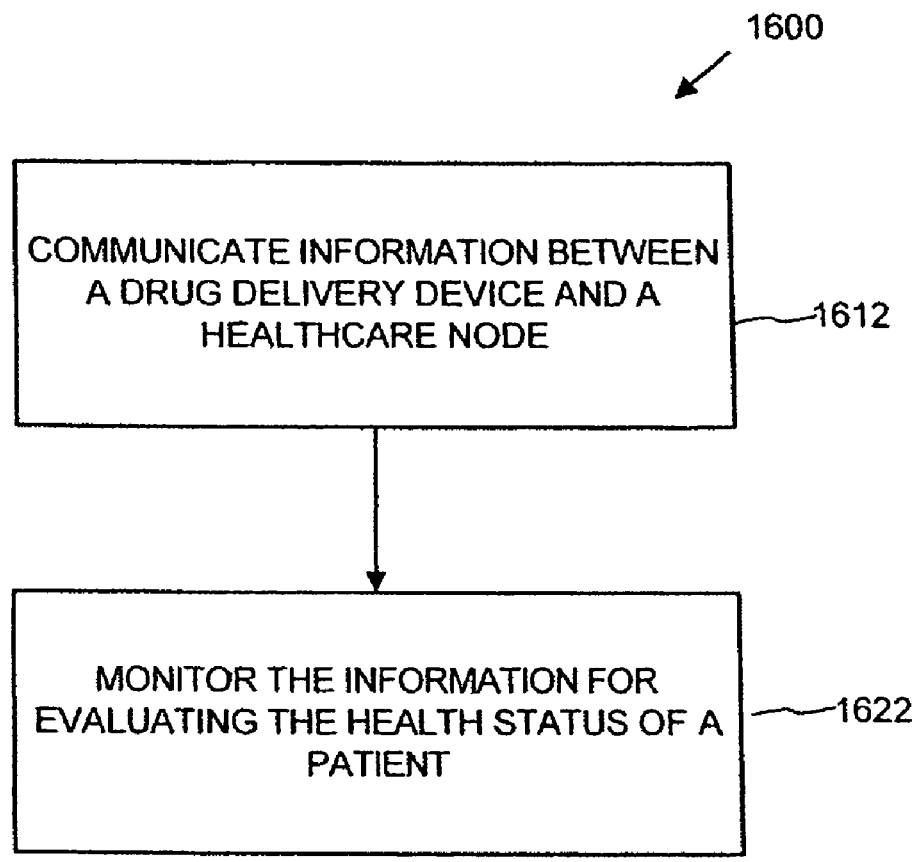
FIG. 16 is a flowchart showing an exemplary method for operating a healthcare system having a plurality of nodes.

FIG. 16 shows an exemplary method 1600 for operating a healthcare system with a plurality of healthcare nodes, according to one embodiment. The method 1600 can be performed, for example, by the system 1000 of FIG. 10 or the system 1100 of FIG. 11.

At 1612, information is communicated between a drug delivery device having at least one jet dispenser and a smart device that is coupled to another node in the healthcare system. The communication can be two-way or one way between the drug delivery device and a healthcare node. The information can be communicated via wireless networking, infrared, radio waves, or any other form of communication. Proximity devices also can be used in communicating the information between the drug delivery device and the health care node. The information can include, but is not limited to, bioactive composition data, human subject data, computerized support system data and medical device data At 1622, the information is monitored for evaluating the health status of a patient. Monitoring the information provides healthcare nodes real-time data which can be crucial in evaluating the health status of a patient. For example, real-time data enables healthcare professionals to monitor a patient's drug delivery and response to the drug based upon vital sign information.

Figure 17:
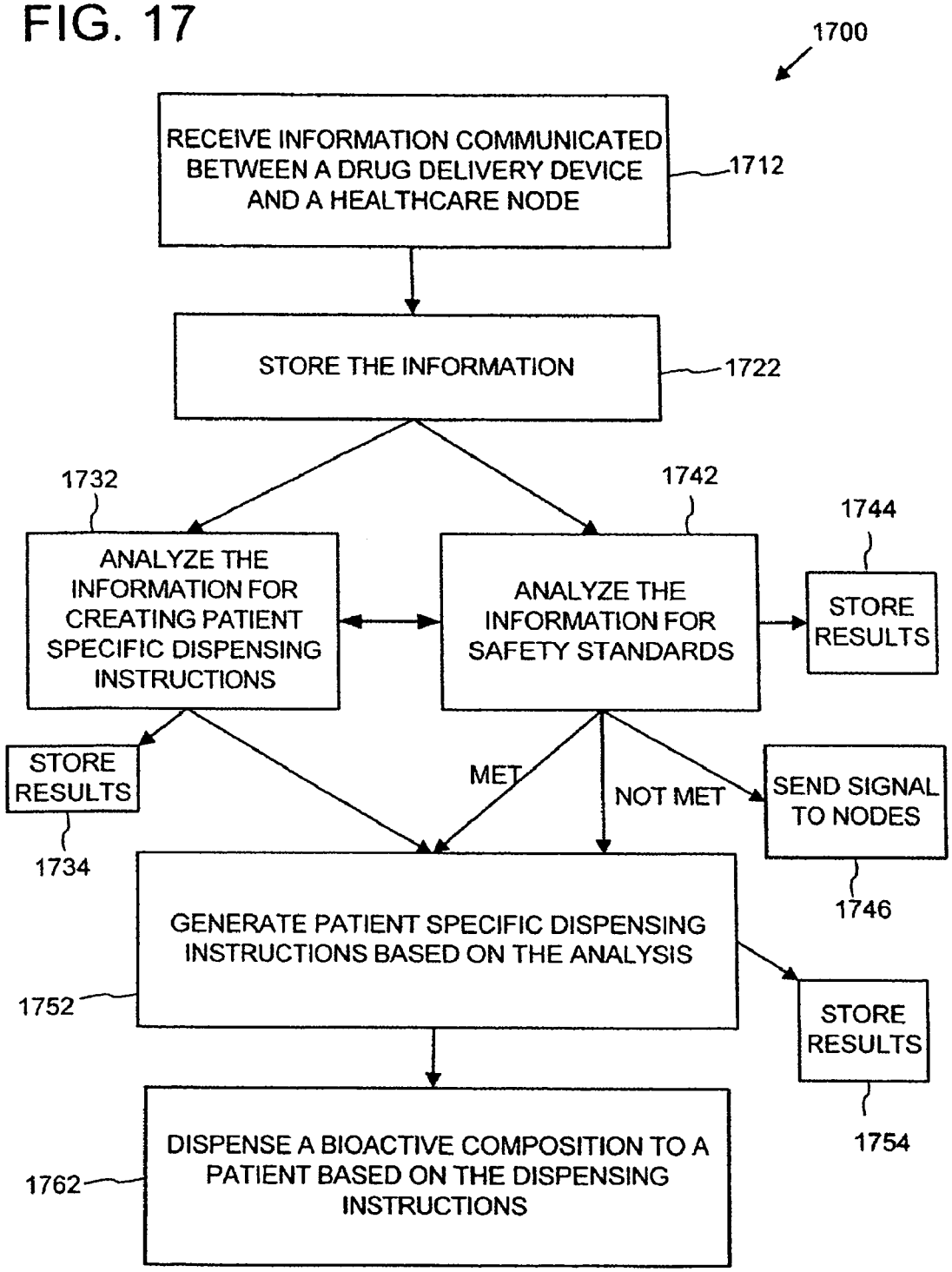
FIG. 17 is a flowchart showing an exemplary method for monitoring information communicated between healthcare nodes for evaluating the health status of a patient.

FIG. 17 is a flowchart showing an exemplary method 1700 for monitoring information (for example, the step of monitoring information indicated at 1622 in FIG. 16) communicated between healthcare nodes for evaluating the health status of a patient, according to one embodiment. The method 1700 can be performed, for example, by the system 1000 of FIG. 10 or the system 1100 of FIG. 11.

At 1712, information communicated between a drug delivery device and a health care node is received by respective smart devices coupled to the drug delivery device and health care node.

At 1722, the information is stored. For example, the information can be stored on the smart device coupled to the drug delivery device and/or forwarded to another health care node smart device, such as a computer system or smart device, for storage.

At 1732, the information is analyzed for creating or modifying patient-specific dispensing instructions. For example, patient vital signs or medical history can be analyzed and dispensing instructions can be modified accordingly.

At 1734, the analysis is stored.

At 1742, the information is analyzed for compliance with predetermined safety standards. This can include standards for patient vital signs, drug compliance, drug delivery device operation, and any other safety checks and balances.

At 1744, the analysis for compliance with predetermined safety standards is stored.

At 1746, a signal is communicated to one or more healthcare nodes that a predetermined safety standard was not met.

At 1752, patient-specific dispensing instructions are generated based on at least one of the analyzing steps 1732 and 1742. If the safety standards are met, then instructions are generated based on the analysis 1732. If safety standards are not met, then instructions are generated to stop dispensing the bioactive composition and lock down the device.

At 1762, the bioactive composition is dispensed to the patient based on the generated instructions.

Figure 18:
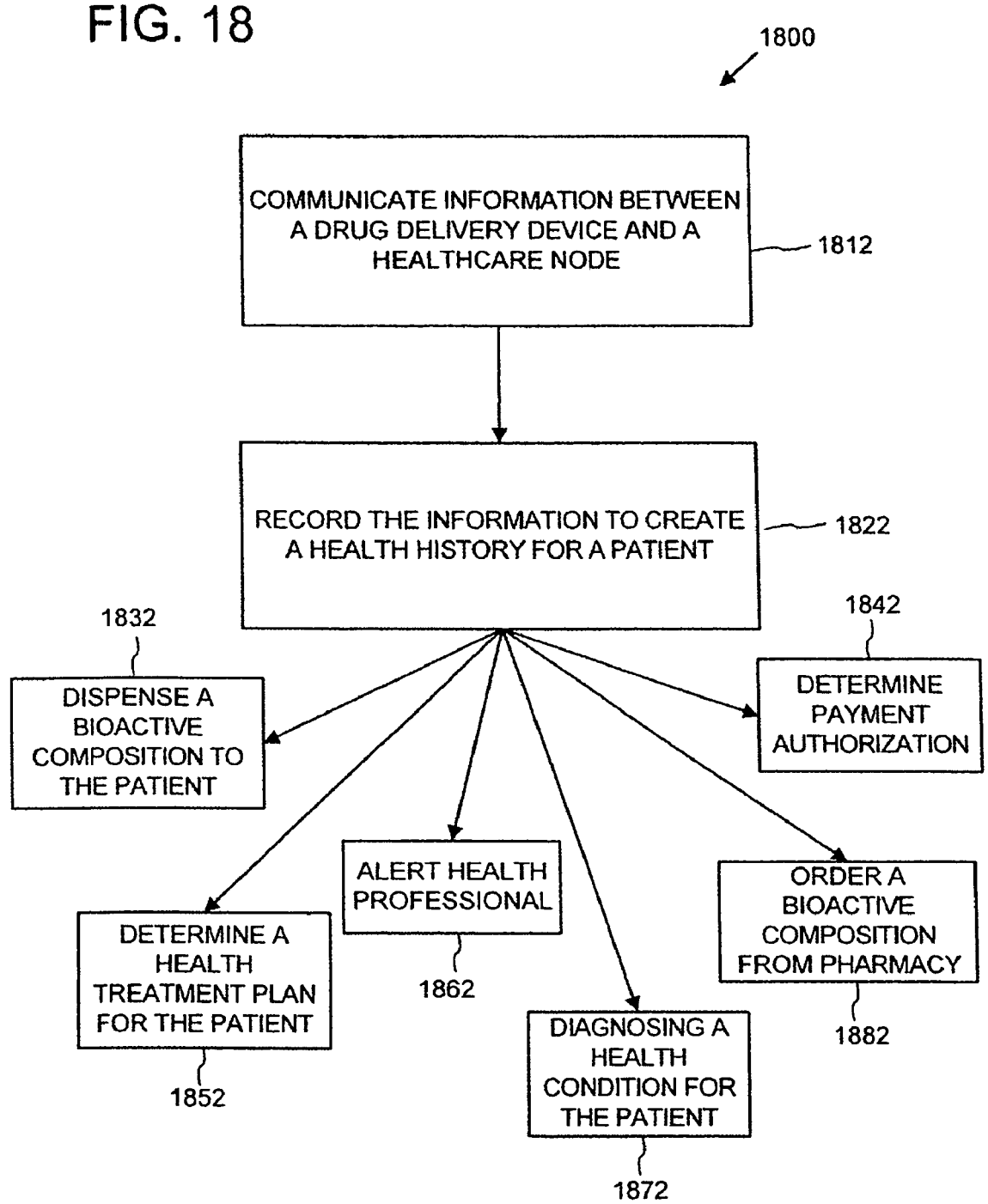
FIG. 18 is a flowchart showing another exemplary method for operating a healthcare system having a plurality of nodes.

FIG. 18 is a flowchart showing another exemplary method 1800 for operating a healthcare system with a plurality of nodes, according to one embodiment. The method 1800 can be performed, for example, by the system 1000 of FIG. 10 or the system 1100 of FIG. 11.

At 1812, information is communicated between a drug delivery device having at least one jet dispenser and a smart device that is coupled to another node in the healthcare system. The information can be communicated via wireless networking, infrared, radio waves, or any other form of communication. Proximity devices also can be used in communicating between the drug delivery device and the health care node. The information can include, but is not limited to, bioactive composition data, human subject data, computerized support system data and medical device data At 1822, the information that is communicated is recorded to create a health history for a patient. For example, the information can be recorded on a centralized computer system, such as an electronic medical record system, and/or other healthcare nodes having data-recording capabilities.

At 1832, the health history information can be accessed for use in dispensing a bioactive composition from the drug delivery device to the patient. Such information can be valuable in setting predetermined patient-specific safety levels, in addition to determining a customized therapy curve (i.e. plan) for a patient. A customized therapy plan for a patient can include dispensing instructions that increases or decreases the dispensing rate of one or more drugs based on time of day, day of the week, patient vital signs, and/or various other parameters. A customized therapy plan can therefore have a predetermined, prescribed customized therapy plan, and such a plan can be adjusted during treatment based on information received from healthcare nodes within the system.

At 1842, payment authorization can be determined for drugs and procedures based upon access to the recorded health history information.

At 1852, a health treatment plan for the patient can be determined based on the upon the recorded health history information. For example, a health treatment plan can include a schedule or plan of monitoring and/or actively adjusting the health status of a patient in order to monitor or treat a disease or other ailment.

At 1862, health professionals can be alerted when the recorded information satisfies a predetermined condition (for example, health warning information, vital sign information within a certain range, etc.), as well as when safety concerns occur when real-time data is compared to the recorded information.

At 1872, a health condition for a patient can be diagnosed or confirmed based up the recorded health history of the patient.

At 1882, a bioactive composition can be automatically ordered from a pharmacy (for example, when a fluid repository is running low and that information is recoded) based on access to the recorded health history of the patient.

Additionally, the recorded information can be used for various other tasks in the healthcare field.

FIG. 19 is a flowchart showing an exemplary implementation 1900 of a system and method for operating a healthcare system. In this example, the system is described in connection with an infusion device, such as infusion devices described in FIGS. 1-9, but other drug delivery devices can be used to administer a bioactive composition to a patient. In such an example, operating efficiency and speed of communication is improved over existing systems and methods, while also improving patient care with increased safety and personalized drug therapy administration (i.e. customized therapy curves and the like).

In this example, at 1912 a doctor wearing or carrying a smart device, or having an embedded smart device, determines a bioactive composition prescription 1914 for a patient 1942. The prescription can be ordered through a CPOE and/or an electronic medical records system. The prescription can include the type and amount of drug, and other details relating to the administration of the drug (for example, details such as the time and day of administration and instructions for varying drug distribution based on such, and the like), which can create customized therapy curves.

At 1916, upon ordering the prescription, a computer system can conduct a safety check in which a search of the medical history of patient 1942 can be conducted to determine if there are any safety issues such as allergies, drug identities, dosage mistakes, and similar prescription error safety checks. Should a safety issue be recognized, the computer system can communicate with the doctor via the doctor's smart device. After the doctor has had the chance to review the safety issue, the doctor can manually override the safety check and keep the initial prescription or adjust the prescription and reorder if that is appropriate. Should a safety issue not be recognized or the doctor manually overrides the safety check, the details about the prescription such as the bioactive composition identity, dosage amount, dosage rate, dosage frequency and dosage ratio can be forwarded on to a smart device associated with the patient and/or a smart device associated with the pharmacist 1922.

At 1924, the pharmacist fills the order by filling a fluid reservoir 1926 with the prescribed bioactive composition and/or locating a disposable fluid reservoir already containing the prescribed bioactive composition. In some embodiments, the pharmacist's smart device can be in contact with a computer system that verifies that the drug is covered under the patient's medical insurance. Should it not be covered, or there is a cheaper, suitable alternative, this information can be forwarded to the doctor's smart device for a request to reorder the prescription for the alternative drug, at which point the foregoing steps can be repeated for the alternative drug.

At 1932, the fluid reservoir 1926 can be transferred to the location of the patient 1942 by a nurse or other medical staff. The fluid reservoir can be coupled to a smart device which can include data such as bioactive composition data, safety data, expiration data (e.g., expiration time or date), prescribed dosage amount, prescribed dosage rate, prescribed dosage frequency, prescribed dosage ratio, patient identification data, and/or various other types of data relating to the prescription and/or the patient's health.

At 1944, a safety query can be initiated between the smart devices of the fluid reservoir 1926 and the patient 1942. Comparisons can be made of the information stored in the smart devices. For example, details about the prescription (i.e. data stored on the patient's smart device and or any other smart device) and what is actually present in the fluid reservoir (data stored on the fluid reservoir's smart device) can be compared. The data compared can include the following: dosage amount, rate, frequency, and ratio versus those that were prescribed. Additionally, to confirm that the right person is to receive the bioactive composition, the patient identification, as well as the pharmacist, nurse and/or doctor identifications can be verified.

At 1946, instructions are communicated to the drug delivery device 1950 to deliver the drug, in the event that the safety query is determined to be okay.

At 1948, an alarm signal can be communicated from the smart device on the patient, fluid reservoir, and/or drug delivery device 1950 to one or more of the other healthcare nodes in the system, in the alternative event that the safety query is not okay. Additionally, in most cases, the drug delivery device 1950 can be "locked down," (i.e. instructed to do such) so that it cannot be operated until the safety issue is addressed. For example, if the patient identification on stored on the patient's smart device did not match the patient identification stored on the fluid reservoir smart device, then an alarm signal can be communicated to other healthcare nodes in the system and the drug delivery device "locked down" to ensure that the wrong drug is not administered to the wrong patient.

At 1954, additional safety checks can be performed. Such checks can include querying data stored on computer systems, including data such as patient medical information and health history. For example, an electronic medical record system can be queried for data comparison safety checks, as well as computer systems with decision support system information and payment provider information. Safety checks can also include analyzing the bioactive composition safety data, expiration date data and time data stored on any variety of smart devices and computer systems. Furthermore, real-time vital signs data and data from the drug delivery device can be analyzed both before and during drug administration for safety and the possibility of adjusting the delivery of the bioactive composition in real time, such as by increasing or decreasing the rate at which the bioactive composition is being delivered to the patient.

At 1952, the bioactive composition (or drug) is administered to the patient 1942, should the safety checks 1954 be determined to be okay. In the alternative, if the safety checks 1954 are determined to be not okay, an alarm signal can be sent to the drug delivery device to stop dispensing the bioactive composition as described at 1948 above.

At 1962, vital signs data and drug delivery device data received from a medical device 1960 that analyzes the patient (for example, medical devices 1132 of FIG. 11) can be stored and communicated between the drug delivery device 1950 and other healthcare nodes. For example, such data 1962 can be communicated via smart devices to the doctor 1912, and/or other nodes in the healthcare system such as nurses, other medical staff, and computer systems. Importantly, the data 1962 can be used by the drug delivery device 1950 to automatically "on-the-fly" (i.e. in real time) adjust the bioactive composition dosage being administered to the patient.

Adjustment of the dosage can be made, for example, by 1) adjusting the frequency of drops of the drug being ejected into the IV line of the patient by the jet dispenser, and/or 2) if an intravenous pump is used to pump saline and bioactive composition mixtures into a patient, adjusting the output of the intravenous pump. Typically, peristaltic pumps are used for pumping saline and bioactive composition mixtures into a patient. Such pumps, however, can't adjust the frequency of drops of drug being ejected into the IV line of the patient. Adjustments to the flow rate of the saline line of a peristaltic pump can result in more of a peristaltic, bolus-effect curve of drug administration, which is not desired. Such peristaltic pump systems, therefore, do not readily lend themselves to providing smooth, infinitely variable, customized therapy curves. Alternatively, adjustments of the frequency of drops distributed by the jet dispenser can produce infinitely variable, smooth therapy curves for the patient. In other words, smooth, personalized, and optionally real-time drug administration is obtained. The doctor 1912 and other medical staff could also manually adjust the instructions for drug delivery or even cancel the drug delivery administration and/or prescribe 1914 new medication starting the process over again.

FIG. 20 and the following discussion provide a brief, general description of a suitable computing environment for any of the methods (for example, software and computer programs) described above and any computer system used in a healthcare system. The methods described above can be implemented in computer-executable instructions organized in program modules. The program modules can include the routines, programs, objects, components, and data structures that perform the tasks and implement the data types for implementing the techniques described above.

While FIG. 20 shows a typical configuration of a desktop computer, the technologies may be implemented in other computer system configurations, including multiprocessor systems, microprocessor-based or programmable consumer electronics, minicomputers, mainframe computers, smart devices, smart cards, and the like. The technologies may also be used in distributed computing environments where tasks are performed in parallel by processing devices to enhance performance. For example, tasks related to measuring characteristics of candidate anomalies can be performed simultaneously on multiple computers, multiple processors in a single computer, or both. In a distributed computing environment, program modules may be located in both local and remote memory storage devices.

The computer system shown in FIG. 20 is suitable for implementing the technologies described herein and includes a computer 2020, with a processing unit 2021, a system memory 2022, and a system bus 2023 that interconnects various system components, including the system memory to the processing unit 2021. The system bus may comprise any of several types of bus structures including a memory bus or memory controller, a peripheral bus, and a local bus using a bus architecture. The system memory includes read only memory (ROM) 2024 and random access memory (RAM) 2025. A nonvolatile system (for example, BIOS) can be stored in ROM 2024 and contains the basic routines for transferring information between elements within the personal computer 2020, such as during start-up. The personal computer 2020 can further include a hard disk drive 2027, a magnetic disk drive 2028, for example, to read from or write to a removable disk 2029, and an optical disk drive 2030, for example, for reading a CD-ROM disk 2031 or to read from or write to other optical media. The hard disk drive 2027, magnetic disk drive 2028, and optical disk drive 2030 are connected to the system bus 2023 by a hard disk drive interface 2032, a magnetic disk drive interface 2033, and an optical drive interface 2034, respectively. The drives and their associated computer-readable media provide nonvolatile storage of data, data structures, computer-executable instructions (including program code such as dynamic link libraries and executable files), and the like for the personal computer 2020. Although the description of computer-readable media above refers to a hard disk, a removable magnetic disk, and a CD, it can also include other types of media that are readable by a computer, such as magnetic cassettes, flash memory cards, digital video disks, and the like.

A number of program modules may be stored in the drives and RAM 2025, including an operating system 2035, one or more application programs 2036, other program modules 2037, and program data 2038. A user may enter commands and information into the personal computer 2020 through a keyboard 2040 and pointing device, such as a mouse 2042. Other input devices (not shown) may include a microphone, joystick, game pad, satellite dish, scanner, or the like. These and other input devices are often connected to the processing unit 2021 through a serial port interface 2046 that is coupled to the system bus, but may be connected by other interfaces, such as a parallel port, game port, or a universal serial bus (USB). A monitor 2047 or other type of display device is also connected to the system bus 2023 via an interface, such as a display controller or video adapter 2048. In addition to the monitor, personal computers typically include other peripheral output devices (not shown), such as speakers and printers. Furthermore, pci slots (not shown) can be used for integration of the above computer system with any of the apparatuses described.

The above computer system is provided merely as an example. The technologies can be implemented in a wide variety of other configurations. In addition, various software aspects can be implemented in hardware, and vice versa.

Any of the methods described herein can be performed by software executed by software in an automated system (for example, a computer system). Fully-automatic (for example, without human intervention) or semi-automatic operation (for example, computer processing assisted by human intervention) can be supported. User intervention may be desired in some cases, such as to adjust parameters or consider results.

Such software can be stored on one or more computer-readable media comprising computer-executable instructions for performing the described actions.

Having illustrated and described the principles of the invention in exemplary embodiments, it should be apparent to those skilled in the art that the described examples are illustrative embodiments and can be modified in arrangement and detail without departing from such principles. For example, in addition to nodes located within a healthcare facility, healthcare nodes can also include nodes in a patient's home and thereby allow for safe and efficient home healthcare options by remote monitoring through wide-area network communication between smart devices. Security measures and authorizations can also be implemented within any of the described methods and systems. For example, passwords and/or encrypted data transfer methods can be utilized to gain access to devices and/or the information communicated between healthcare nodes.

In view of the many possible embodiments to which the principles of the invention may be applied, it should be understood that the illustrative embodiments are intended to teach these principles and are not intended to be a limitation on the scope of the invention. We therefore claim as our invention all that comes within the scope and spirit of the following claims and their equivalents.

We claim:

1. A healthcare system for administering a bioactive composition to a subject, comprising:
    an infusion drug delivery device;
    a first smart device integral with and coupled to the drug delivery device;
    a second smart device coupled to a healthcare node of the healthcare system, wherein the first smart device and the second smart device are operable to communicate with each other information for the administration of the bioactive composition, and wherein the first smart device is configured to automatically create a patient-specific variable drug dosage instruction based at least upon the information received from the second smart device; and
    at least one jet dispenser of the drug delivery device configured to be operable in accordance with the patient-specific variable drug dosage instruction.

2. The system of claim 1, wherein the drug delivery device further comprises a fluid manifold having at least one mixing chamber, the at least one mixing chamber being configured to receive the bioactive composition dispensed from the at least one jet dispenser, the at least one mixing chamber having an inlet for receiving an infusion liquid to be mixed with the bioactive composition and an outlet for discharging a mixture of the infusion liquid and the bioactive composition.

3. The system of claim 1, wherein the drug delivery device further comprises at least one mixing chamber, comprising:
    a drip surface;
    a first inlet for receiving an infusion liquid oriented such that the infusion liquid is directed onto the drip surface;
    a second inlet for receiving the bioactive composition dispensed from the at least one jet dispenser such that the bioactive composition is directed onto the drip surface; and
    a fluid outlet for discharging the mixture of the infusion liquid and the bioactive composition.

4. The system of claim 1, wherein the drug delivery device further comprises at least one fluid reservoir for containing the bioactive composition, the at least one fluid reservoir being fluidly connected to the respective at least one jet dispenser.

5. The system of claim 1, wherein the drug delivery device further comprises at least one drop detector operable to detect at least one characteristic of the droplets of the bioactive composition that are dispensed from the at least one jet dispenser and provide a signal corresponding to the detected at least one characteristic.

6. The system of claim 5, wherein the at least one drop detector is operable to detect a presence of droplets dispensed from the at least one jet dispenser.

7. The system of claim 5, wherein the at least one drop detector is operable to detect a rate at which the drops are ejected from the at least one jet dispenser.

8. The system of claim 5, wherein the at least one drop detector is operable to detect a volume of the droplets dispensed from the at least one jet dispenser.

9. The system of claim 5, wherein the drug delivery device further comprises an alarm operatively connected to the at least one drop detector and operable to provide a warning if the at least one characteristic detected by the drop detector does not satisfy a predetermined condition.

10. The system of claim 9, wherein the alarm provides a warning if the at least one drop detector does not detect the presence of droplets.

11. The system of claim 5, wherein the first smart device comprises a controller operable to control the at least one jet dispenser to dispense the bioactive composition.

12. The system of claim 11, wherein the controller is in communication with the at least one drop detector.

13. The system of claim 11, wherein the controller is operable to automatically shut off the drug delivery device when the information does not comply with predetermined safety standards.

14. The system of claim 1, wherein the at least one jet dispenser comprises a piezoelectric droplet jet dispenser.

15. The system of claim 1, wherein the at least one jet dispenser comprises a thermal droplet jet dispenser.

16. The system of claim 1, wherein the first smart device comprises a smart chip.

17. The system of claim 1, wherein the second smart devise comprises a smart chip.

18. The system of claim 17, wherein the health care node comprises a human body and the second smart device is embedded within the human body.

19. The system of claim 17, further comprising a wearable mounting device for mounting the second smart device.

20. The system of claim 19, wherein the mounting device comprises a band adapted to be worn by a person.

21. The system of claim 1, wherein the healthcare node comprises a person.

22. The system of claim 21, wherein the person comprises at least one person selected from the group consisting of:
    a patient;
    a doctor;
    a nurse;
    a pharmacist; and
    a laboratory technician.

23. The system of claim 1, wherein the healthcare node comprises a computer system.

24. The system of claim 23, wherein the computer system comprises at least one system selected from the group consisting of:
    a decision support system;
    a electronic medical record system; and
    a medical payment provider system.

25. The system of claim 1, wherein the healthcare node comprises at least one node selected from the group consisting of:
    a fluid reservoir for containing the bioactive composition; and
    a medical device.

26. The system of claim 25, wherein the medical device is operable to detect patient vital signs.

27. The system of claim 1, wherein the information for the administration of the bioactive composition comprises at least one type of data selected from the group consisting of:
    bioactive composition data;
    patient or health professional data;
    computerized support system data; and
    medical device data.

28. The system of claim 27, wherein the information for the administration of the bioactive composition is stored on a computer system to create a health history for the subject.

29. The system of claim 27, wherein the bioactive composition data comprises at least one type of data selected from the group consisting of:
    fluid reservoir data;
    bioactive composition identification data;
    bioactive composition dosage amount data;
    bioactive composition dosage rate data;
    bioactive composition dosage frequency data; and
    bioactive composition dosage ratio data.

30. The system of claim 29, wherein the fluid reservoir data comprises at least one type of data selected from the group consisting of:
    bioactive composition safety data;
    bioactive composition expiration date data;
    bioactive composition expiration time data;
    prescribed bioactive composition dosage amount data;
    prescribed bioactive composition dosage rate data;
    prescribed bioactive composition dosage frequency data; and
    prescribed bioactive composition dosage ratio data.

31. The system of claim 27, wherein the patient or healthcare professional data comprises at least one type of data selected from the group consisting of:
    patient identification data;
    doctor identification data;
    nurse identification data; and
    pharmacist identification data.

32. The system of claim 27, wherein the computerized support system data comprises as least one type of data selected from the group consisting of:
    payment provider information;
    patient medical information; and
    decision support system information.

33. The system of claim 27, wherein the medical device data comprises patient vital signs data.

34. They system of claim 27, wherein the medical device data comprises an alarm signal.

35. A method for administering a bioactive composition to a subject from an infusion drug delivery device having at least one jet dispenser, comprising:
    detecting, via a smart device integral with and coupled to the drug delivery device, at least one smart device coupled to a healthcare node;
    receiving information from the at least one smart device relating to the administration of the bioactive composition;
    creating, via the smart device coupled to the drug delivery device, a subject-specific variable drug dosage instruction for the administration of the bioactive composition to the subject based on the information received;
    communicating the subject-specific variable drug dosage instruction to the at least one jet dispenser of the drug delivery device; and
    dispensing the bioactive composition from at least one jet dispenser of the drug delivery device in accordance with the subject-specific variable drug dosage instruction.

36. The method of claim 35, wherein the at least one smart device coupled to the healthcare node comprises a smart chip.

37. The method of claim 35, wherein the drug delivery device further comprises a controller operable to control the at least one jet dispenser to dispense the bioactive composition.

38. The method of claim 35, wherein detecting the at least one smart device coupled to the healthcare node comprises detecting the at least one smart device via wireless communication.

39. The method of claim 35, wherein the act of receiving information comprises receiving information via wireless communication.

40. The method of claim 35, wherein the at least one healthcare node comprises at least one node selected from the group consisting of:
- a person;
- a computer system;
- a fluid reservoir for containing the bioactive composition; and
- a medical device.

41. The method of claim 35, wherein the information received from the at least one smart device coupled to the healthcare node comprises at least one type of data selected from the group consisting of:
- bioactive composition data;
- patient or healthcare professional data;
- computerized support system data; and
- medical device data.

42. The method of claim 35, further comprising creating a health history for the subject from the information received from the at least one smart device coupled to the healthcare node.

43. The method of claim 35, wherein creating the subject-specific variable drug dosage instruction comprises:
- analyzing the information received from the at least one smart device coupled to the healthcare node; and
- creating the subject-specific variable drug dosage instruction based on the analyzing.

44. The method of claim 43, wherein the act of analyzing the information received comprises comparing the information received.

45. The method of claim 43, wherein the act of creating the subject-specific variable drug dosage instruction comprises:
- determining whether the information satisfies predetermined safety standards; and
- creating the subject-specific variable drug dosage instruction based upon the act of determining whether the information satisfies predetermined safety standards.

46. The method of claim 45, further comprising customizing the subject-specific variable drug dosage instruction for the subject based on the information received.

47. The method of claim 45, wherein the act of creating the subject-specific variable drug dosage instruction based upon the act of determining whether the information satisfies predetermined safety standards comprises generating instructions to stop dispensing the bioactive composition from the drug delivery device if safety standards are not met.

48. The method of claim 45, wherein the act of creating the subject-specific variable drug dosage instruction based upon the act of determining whether the information satisfies predetermined safety standards comprises generating instruction to dispense the bioactive compositions from the drug delivery device if safety standards are met.

49. The method of claim 35, wherein the act of creating a health history of a subject comprises storing the administration instructions on a computer system.

50. The method of claim 35, wherein the act of communicating the subject-specific variable drug dosage instruction comprises communicating the subject-specific variable drug dosage instruction via wireless communication.

* * * * *

UNITED STATES PATENT AND TRADEMARK OFFICE
CERTIFICATE OF CORRECTION

| | | |
|---|---|---|
| PATENT NO. | : 7,819,847 B2 | Page 1 of 1 |
| APPLICATION NO. | : 11/228884 | |
| DATED | : October 26, 2010 | |
| INVENTOR(S) | : Christopher John Vitello et al. | |

It is certified that error appears in the above-identified patent and that said Letters Patent is hereby corrected as shown below:

In column 28, line 33, in Claim 32, delete "as" and insert -- at --, therefor.

Signed and Sealed this
Twentieth Day of December, 2011

David J. Kappos
*Director of the United States Patent and Trademark Office*